United States Patent
Raicu et al.

(10) Patent No.: US 9,103,721 B2
(45) Date of Patent: *Aug. 11, 2015

(54) HIGH SPEED MICROSCOPE WITH SPECTRAL RESOLUTION

(75) Inventors: Valerica Raicu, Shorewood, WI (US); Gabriel Biener, Shorewood, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 321 days.

This patent is subject to a terminal disclaimer.

(21) Appl. No.: 13/439,951

(22) Filed: Apr. 5, 2012

(65) Prior Publication Data

US 2012/0257196 A1    Oct. 11, 2012

Related U.S. Application Data

(60) Provisional application No. 61/472,761, filed on Apr. 7, 2011, provisional application No. 61/480,083, filed on Apr. 28, 2011.

(51) Int. Cl.
*G01J 3/00*     (2006.01)
*G01J 3/28*     (2006.01)
(Continued)

(52) U.S. Cl.
CPC .............. *G01J 3/2803* (2013.01); *G01J 3/027* (2013.01); *G01J 3/0294* (2013.01); *G01J 3/06* (2013.01); *G01J 3/4406* (2013.01); *G02B 21/002* (2013.01); *G02B 21/0076* (2013.01);
(Continued)

(58) Field of Classification Search
CPC ................. G01J 3/02; G01J 3/28; G01J 3/42; G01J 21/31; G01J 21/551

USPC ................................... 356/300, 326–328, 334
See application file for complete search history.

(56) References Cited

U.S. PATENT DOCUMENTS

| 4,407,008 A | 9/1983 | Schmidt et al. |
| 5,034,613 A | 7/1991 | Denk et al. |

(Continued)

FOREIGN PATENT DOCUMENTS

WO     0042417     7/2000

OTHER PUBLICATIONS

Abbott Molecular, "Genetics," Copyright © 2012 Abbott Laboratories. Abbott Park, Illinois, U.S.A., http://www.abbottmolecular.com/products/genetics.html.

(Continued)

*Primary Examiner* — Abdullahi Nur
(74) *Attorney, Agent, or Firm* — Michael Best & Friedrich LLP

(57) ABSTRACT

A system and method of high-speed microscopy using a two-photon microscope with spectral resolution. The microscope is operable to provide two- to five-dimensional fluorescence images of samples, including two or three spatial dimensions, a spectral dimension (for fluorescence emission), and a temporal dimension (on a scale of less than approximately one second). Two-dimensional (spatial) images with a complete wavelength spectrum are generated from a single scan of a sample. The microscope may include one of a multi-beam point scanning microscope, a single beam line scanning microscope, and a multi-beam line scanning microscope. The line scans may be formed using one or more of curved mirrors and lenses. The multiple beams may be formed using one of a grating, an array of lenses, and a beam splitter.

34 Claims, 24 Drawing Sheets

(51) Int. Cl.
| | |
|---|---|
| G02B 21/00 | (2006.01) |
| G01J 3/02 | (2006.01) |
| G01J 3/06 | (2006.01) |
| G01J 3/44 | (2006.01) |
| G02B 21/16 | (2006.01) |
| G02B 27/09 | (2006.01) |

(52) U.S. Cl.
CPC ........... *G02B 21/16* (2013.01); *G02B 27/0927* (2013.01); *G02B 27/0983* (2013.01)

(56) References Cited

U.S. PATENT DOCUMENTS

| | | | |
|---|---|---|---|
| 5,192,980 | A | 3/1993 | Dixon et al. |
| 5,883,385 | A | 3/1999 | Takahashi et al. |
| 6,028,306 | A | 2/2000 | Hayashi |
| 6,088,097 | A | 7/2000 | Uhl |
| 6,134,002 | A | 10/2000 | Stimson et al. |
| 6,344,653 | B1 | 2/2002 | Webb et al. |
| 6,388,746 | B1 | 5/2002 | Eriksson et al. |
| 6,449,039 | B1 | 9/2002 | Bouzid |
| 6,477,327 | B1 | 11/2002 | Imai |
| 6,603,537 | B1 | 8/2003 | Dietz et al. |
| 6,809,815 | B2 | 10/2004 | Knebel |
| 7,561,265 | B2 * | 7/2009 | Kobayashi et al. ........... 356/318 |
| 7,973,927 | B2 | 7/2011 | Raicu et al. |
| 8,094,304 | B2 | 1/2012 | Raicu et al. |
| 2002/0109101 | A1 | 8/2002 | Hoffmann |
| 2002/0109840 | A1 | 8/2002 | Wolleschensky et al. |
| 2002/0198457 | A1 | 12/2002 | Tearney et al. |
| 2003/0081299 | A1 | 5/2003 | Suzuki et al. |
| 2003/0098979 | A1 | 5/2003 | Dress et al. |
| 2003/0231825 | A1 * | 12/2003 | Olschewski ................. 385/27 |
| 2005/0111089 | A1 | 5/2005 | Baer |
| 2006/0012891 | A1 | 1/2006 | Goelles et al. |
| 2006/0056468 | A1 | 3/2006 | Dantus et al. |
| 2006/0140462 | A1 | 6/2006 | Saggau et al. |
| 2007/0057211 | A1 | 3/2007 | Bahlman et al. |
| 2007/0247620 | A1 | 10/2007 | Koo |
| 2007/0296973 | A1 | 12/2007 | Kiers et al. |
| 2008/0088838 | A1 | 4/2008 | Raicu et al. |
| 2008/0116392 | A1 | 5/2008 | Brooker |
| 2008/0165358 | A1 | 7/2008 | Engelhardt |
| 2008/0308730 | A1 | 12/2008 | Vizi et al. |
| 2009/0084980 | A1 | 4/2009 | Mertz |
| 2009/0258383 | A1 | 10/2009 | Kovac et al. |
| 2009/0278058 | A1 | 11/2009 | Kim et al. |
| 2010/0176307 | A1 | 7/2010 | Hell et al. |
| 2011/0025831 | A1 | 2/2011 | Bewersdorf et al. |

OTHER PUBLICATIONS

Abbott Molecular, "Oncology," Copyright © 2012 Abbott Laboratories. Abbott Park, Illinois, U.S.A., http://www.abbottmolecular.com/products/oncology.html.
Abbott Molecular, "PathVysion," Copyright © 2012 Abbott Laboratories. Abbott Park, Illinois, U.S.A., http://www.abbottmolecular.com/products/oncology/fish/breast-cancer-pathvysion.html.
Angers, S. et al. "Dimerization: An Emerging Concept for G Protein-Coupled Receptor Ontogeny and Function," Annual Reviews Pharmacology Toxicology, 2002, p. 409-435, vol. 42.
Bacskai, B.J. et al. "Fluorescence Resonance Energy Transfer Determinations using Multiphoton Fluorescence Lifetime Imaging Microscopy to Characterize Amyloid-Beta Plaques," Journal of Biomedical Optics, 2003, p. 368-375, vol. 8, iss. 3.
Chabre, M. et al. "Monomeric G-Protein-Coupled Receptor as a Functional Unit," Biochemistry, 2005, p. 9395-9403, vol. 44, iss.27.
Chen, Y.E. et al. "Characterization of Spectral FRET Imaging Microscopy for Monitoring Nuclear Protein Interactions," Journal of Microscopy, 2007, p. 139-152, vol. 228.
Denk, Winfried, et al., "Two-Photon Laser Scanning Fluorescence Microscopy", Science, New Series, April 6, 1990, p. 73-76, vol. 248, No. 4951.
Edelman, L.M. et al. "Fluorescence Resonance Energy Transfer over ~130 Basepairs in Hyper stable Lac Repressor-DNA Loops," Biophysical Journal, 2003, p. 1131-1145, vol. 84.
Elangovan, M. et al., "Nanosecond Fluorescence Resonance Energy Transfer-Fluorescence Lifetime Imaging Microscopy to Localize the Protein Interactions in a Single Living Cell," Journal of Microscopy, 2002, p. 3-14, vol. 205.
Greenbaum, L. et al., "Chemical Approaches for Functinally Probing the Proteome," Molecular & Cellular Proteomics, (2002), p. 60-68, vol. 1.
Greenbaum, L et al., "Spectrally resolved microscopy of GFP trafficking," J. Histochem. Cytochem. (2002) 50(9): 1205-12.
Gurevich, V. et al., "GPCR Monomers and Oligomers: It Takes All Kinds," Trends in Neurosciences, 2008, p. 74-81, vol. 31, issue 2.
Haraguchi, Tokuko, et al., "Spectral Imaging Fluorescence Microscopy", Genes to Cells, (2002), p. 881-887, vol. 7.
Hern, J. et al. "Formation and Dissociation of M1 Muscarinic Receptor Dimers Seen by Total Internal Reflection Fluorescence Imaging of Single Molecules," PNAS, 2010, p. 2693-2698, vol. 107, iss. 6.
Hoppe, A. et al. "Fluorescence Resonance Energy Transfer-Based Stoichiometry in Living Cells," Biophysical Journal, 2002, p. 3652-3664, vol. 83
Invitrogen, "Cellular Imaging," © 2012 Life Technologies Corporation., http://www.invitrogen.com/site/us/en/home/Products-and-Services/Applications/Cell-Analysis/Cellular-Imaging.html.
Invitrogen, "Drug Discovery and Development," © 2012 Life Technologues Corporation, http://www.invitrogen.com/site/us/en/home/Products-and-Services/Applications/Drug-Discovery.html.
Invitrogen, "Live/Dead Cell Viability Assays," © 2012 Life Technologies Corporation., http://www.invitrogen.com/site/us/en/home/brands/Molecular-Probes/Key-Molecular-Probes-Products/LIVE-DEAD-Viability-Brand-Page.html.
Karpova, T.S. et al. "Fluorescence Resonance Energy Transfer from Cyan to Yellow Fluorescent Protein Detected by Acceptor Photobleaching using Confocal Microscopy and a single laser," Journal of Microscopy, 2003, p. 56-70, vol. 209, iss. 1.
Koushik, S.V. et al. "Cerulean, Venus, and VenusY6&C FRET Reference Standards," Biophysical Journal: Biophysical Letters, 2006, p. L99-L101, vol. 91, iss. 12.
Lakowicz, J. et al. "Plasmonics in Biology and Plasmon-Controlled Fluorescence," Plasmonics, 2006, p. 5-33, vol. 1, iss. 1.
Langmead, C. et al. "Muscarinic Acetylcholine Receptors as CNS Drug Targets," Pharmacology and Therapeutics, 2008, p. 232-243, vol. 117.
Lansford, J. et al., "Resolution of multiple green fluorescent protein color variants and dyes using two-photon microscopy and imaging spectroscopy," Journal of Biomedical Optics, 2001, pp. 311-318, vol 6, iss. 3.
MA, A.W. et al. "Heterooligomers of the muscarinic receptors and G proteins purified from porcine atria," Biochemical and Biophysical Research Communications, 2008, p. 128-133, vol. 374, iss. 1.
Merzlyakov, M. et al. "Studies of Receptor Tyrosine Kinase Transmembrane Domain Interactions: The Excitation-Emission FRET Method," Journal of Membrane Biology, 2007, p. 93-103, vol. 215.
Milligan, G. "G Portein-Coupled Receptor Hetero-Dimerization: Contribution to Pharmacology and Function," British Journal of Pharmacology, p. 5-14, vol. 158.
Mulholland, J. et al. "Visualizatio of Receptor-Mediated Endocytosis in Yeast," Molecular Biology of the Cell, 1999, p. 799-817, vol. 10.
Neher, R. et al., "Applying Spectral Fingerprinting to the Analysis of FRET Images," Microscopy Research and Technique (2001) 64:185-195.
Neher, R. et al., "Optimizing Imaging Parameters for the Separation of Multiple Labels in a Fluorescence Image," Journal of Microscopy (2003) 213: 46-62.
Nielsen, T. et al. "High Efficiency Beam Splitter for Multifocal Multiphoton Microscopy," Journal of Microscopy, 2001, p. 368-376, vol. 201, iss. 3.
Nikon Instruments, "Quantum Dots," © 2012 Nikon Instruments Inc., http://www.nikoninstruments.com/Information-Center/Quantum-Dots.

(56) References Cited

OTHER PUBLICATIONS

Overton, M. et al. "Oligomerization of G-Protein-Coupled Receptors: Lessons from the Yeast *Saccharomyces cerevisiae*," Amercian Society of Microbiology, 2005, p. 1963-1970, vol. 4, iss. 12.

Park, P. et al. "Monomers and Oligomers of the M2 Muscarinic Cholinergic Receptor Purified from Sf9 Cells," Biochemistry, 2003, p. 12960-12971, vol. 42.

Pisterzi, L.F. et al. "Oligomeric Size of the M2 Muscarinic Receptor in Live Cells as Determined by Quantitative Fluorescence Resonance Energy Transfer," The Journal of Biological Chemistry, 2010, p. 16723-16738, vol. 285, iss. 22.

Raicu, V. "Efficiency of Resonance Energy Transfer in Homo-Oligomeric Complexes of Proteins," Journal of Biological Physics, 2007, p. 109-127, vol. 33.

Raicu, V. et al. "Determination of Supramolecular Structure and Spatial Distribution of Protein Complexes in Living Cells," Nature Photonics, 2009, p. 107-113, vol. 3.

Raicu, V. et al. "Protein-Interaction Qualified in vivo by Spectrally Resolved Fluorescence Resonance Energy Transfer," Biochemistry Journal, 2005, p. 265-277, vol. 385.

Raicu, V. et al. "Protein-Protein Interactions," Integrated Molecular and Cellular Biophysics, 2008, p. 195-218, Springer.

Spriet, C. et al. "Enchanced FRET Constrast in Lifetime Imaging," Cytometry Part A, 2008, p. 745-753, vol. 73A.

Stimson, Michael, J., et al., "A Unique Optical Arrangement for Obtaining Spectrally Resolved Confocal Images", Review of Scientific Instruments, Aug. 1999, p. 3351-3354, vol. 70, No. 8.

Sum, S. et al. "Effects of N-Ethylmaleimide on Conformational Equilibria in Purified Cardiac Muscarinic Receptors," The Journal of Biological Chemistry, 2002, p. 36188-36203, vol. 277, iss.39.

Tal, E. et al. "Improved Depth Resolution in Video-Rate Line-Scanning Multiphoton Microscopy using Temporal Focusing," Optics Letters, 2005, p. 1686-1688, vol. 30, iss.13.

Tanke, H.J. et al. "Molecular cytogenetics: unraveling of the genetic composition of individual cells by flurorescence in situ hybridization and digital imaging microscopy," World Journal of Urology, 1995, p. 138-142, vol. 13, iss. 3.

Thaler, C. et al. "Quantitative Multiphoton Spectral Imaging and its Use for Measuring Resonance Energy Transfer," Biophysical Journal, 2005, p. 2736-2749, vol. 89, iss.4.

Tsien, R. "The Green Flourescent Protein," Annual Reviews Biochemistry, 1998, p. 509-544, vol. 67.

Wauters, J. et al. "Fully Automated FISH examination of amniotic fluid cells," Prenatal Diagnosis, 2007, p. 951-955, vol. 27, iss. 10.

Wlodarczyk, J. et al. "Analysis of FRET Signals in the Presence of Free Donors and Acceptors," Biophysical Journal, 2008, p. 986-1000, vol. 94.

Zal, T. et al. "Photobleaching-Corrected FRET Efficiency Imaging of Living Cells," Biohysical Journal, 2004, p. 3923-3939, vol. 86.

Zipfel, W.R. et al. "Nonlinear Magic: Multiphoton Microscopy in the Biosciences," Nature Biotechnology, 2003, p. 1369-1377, vol. 21, iss.11.

International Search Report and Written Opinion for Application No. PCT/US2012/032247 daed Jul. 27, 2012.

Resolution of multiple green fluorescent protein color variants and dyes using two-photon microscopy and imaging spectroscopy, Lansford et al., Journal of Biomedical Optics 6(3), 311-318 (Jul. 2001).

Fully automated FISH examination of amniotic fuid cells. Wauters et al., Prenat Diagn 2007; 27: 951-955. Published online Jun. 29, 2007 in Wiley Interscience.

SLM microscopy: scanless two-photon imaging and photostimulation with spatial light modulators, Nikolenko et al., Frontiers in Neural Circuits, Dec. 19, 2008.

Office Action from the US Patent and Trademark Office for U.S. Appl. No. 13/439,954 dated Aug. 14, 2014 (27 pages).

EP12782196.2 Extended Eurripeen Search Report dated Aug. 19, 2014 (7 pages).

Notice of Allowance from the US Patent Office for U.S. Appl. No. 13/439,958 dated Jan. 22, 2015 (20 pages).

\* cited by examiner

*Multi-Beam Point Scan*

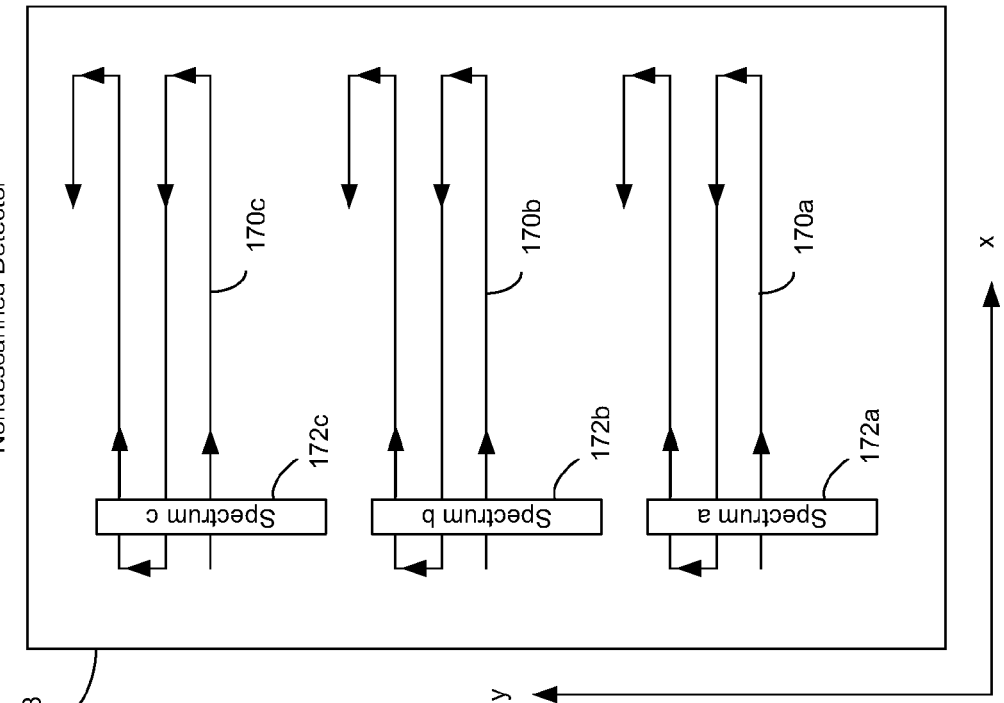
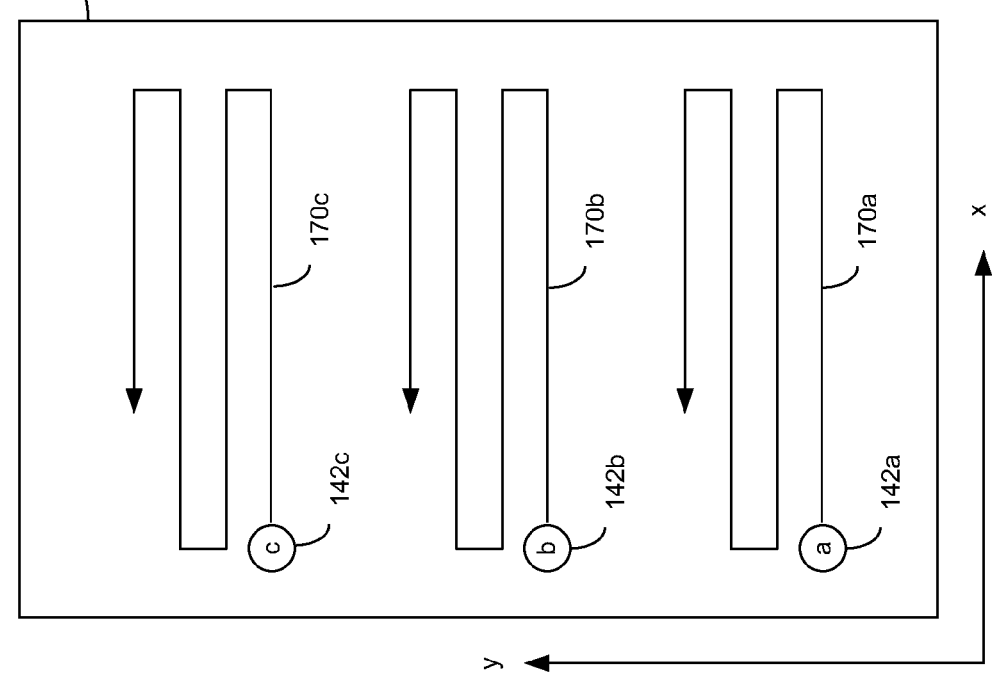

*Single-Beam Line Scan*

*Multi-Beam Line Scan*

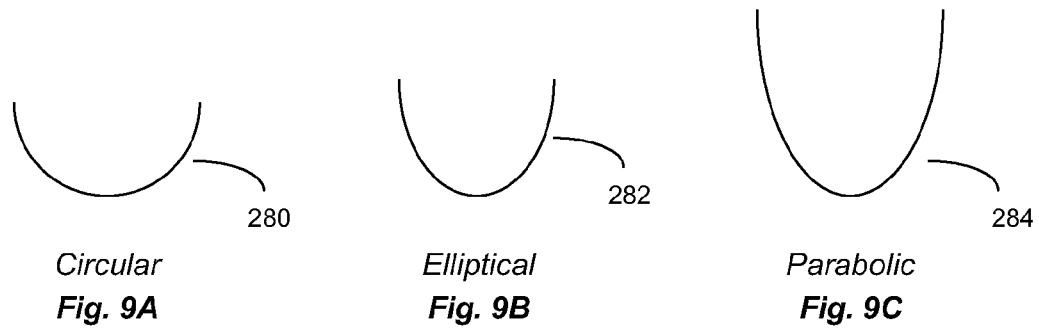
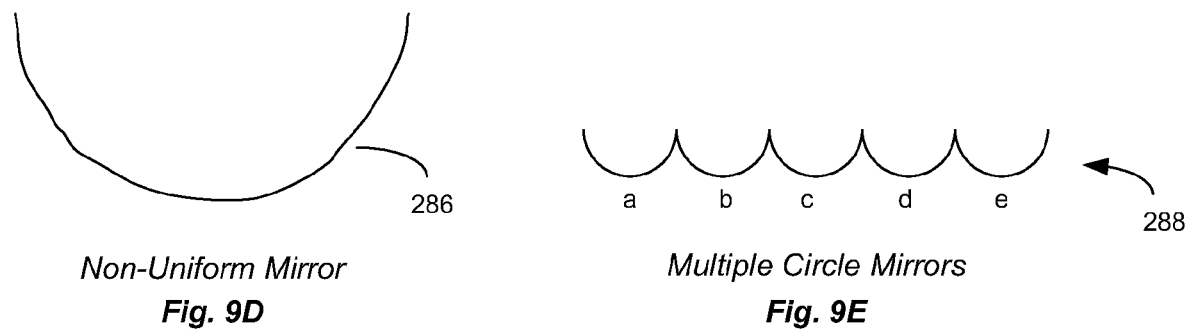
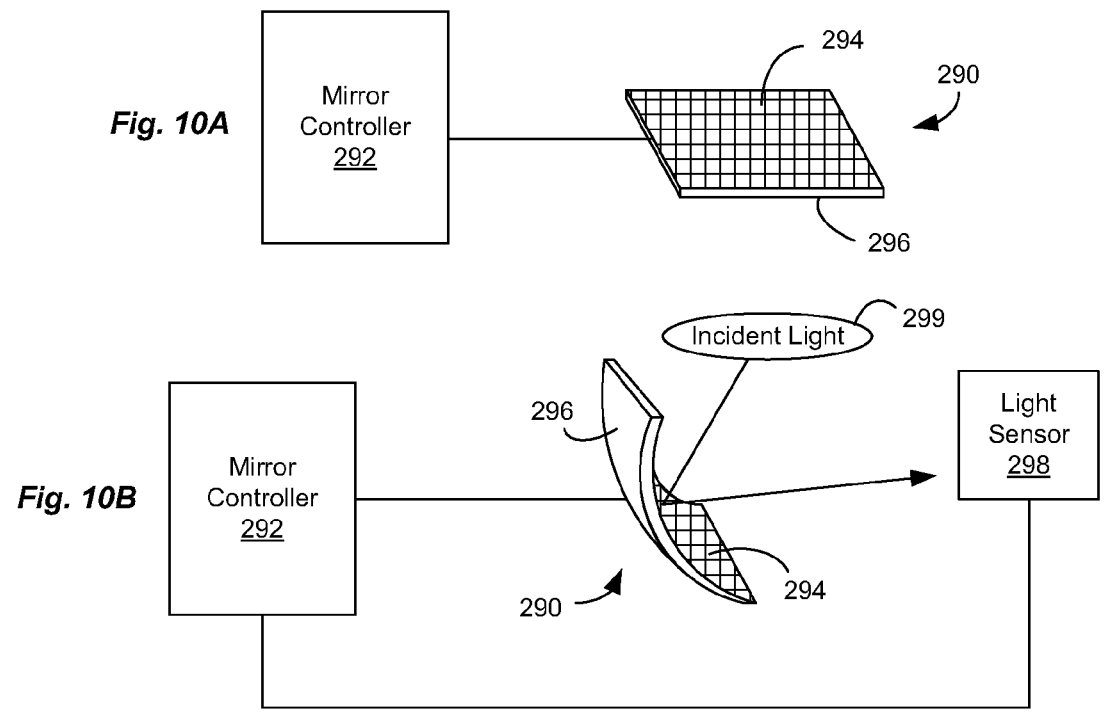

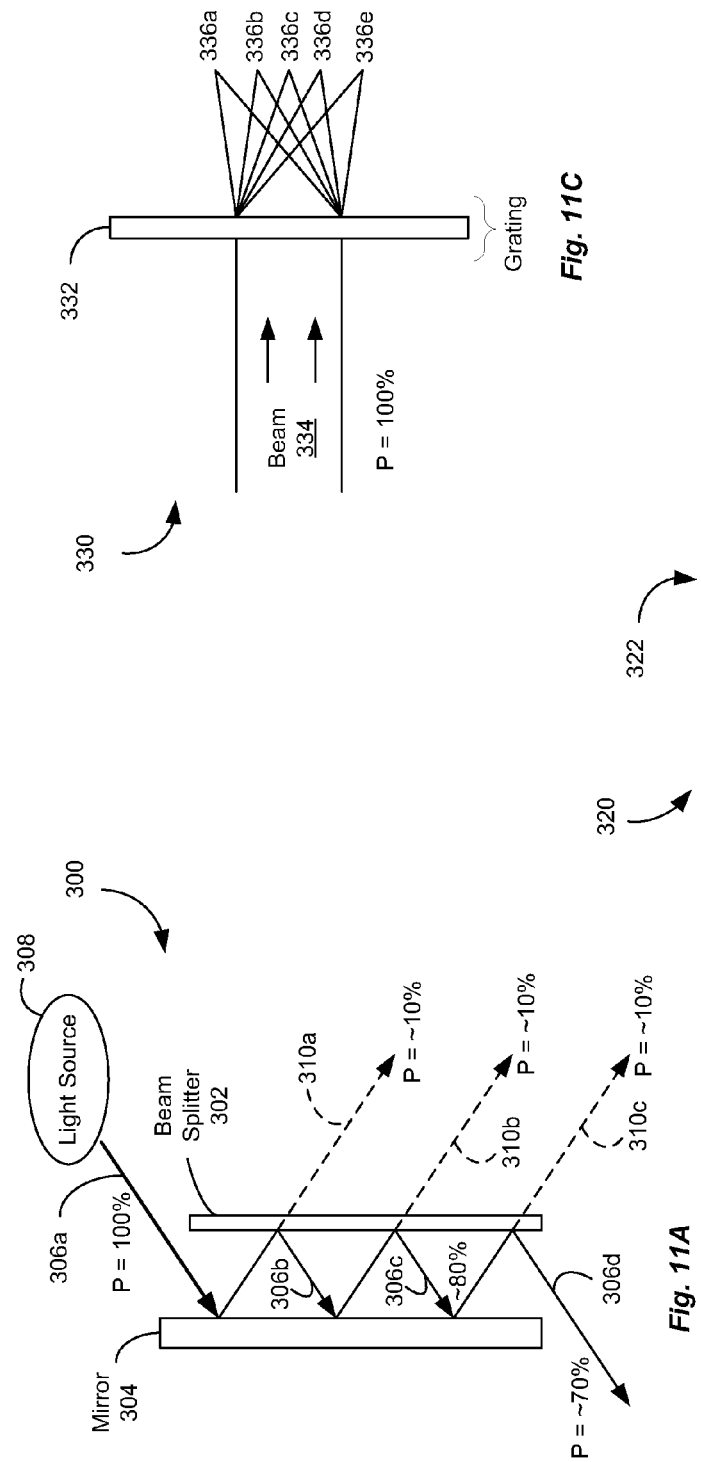
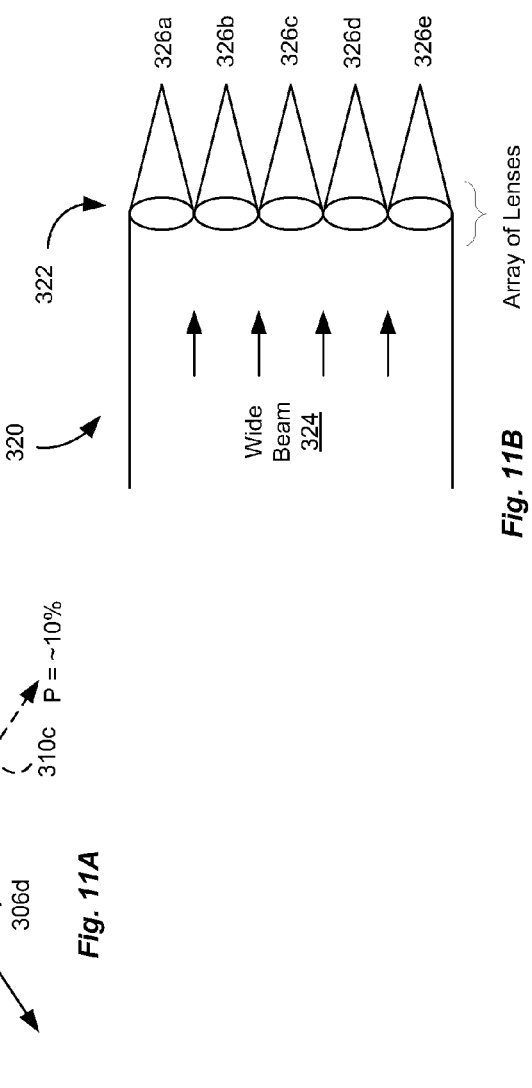
Fig. 11A
Fig. 11B
Fig. 11C

Multi-Beam Point Scan
(Half-Descanned)

*Multi-Beam Point Scan (Descanned)*

Multi-Beam Point Scan
(Half-Descanned)

*Ideal vs. Actual Imprint from Single Beam Point on Detector*

*Actual Light Imprint from Single Beam Point on Detector with Binning*

*No Wavelength Binning*

*Wavelength Binning*

*Transmission Imaging*

*Multi-Wavelength Excitation Beam Scan*

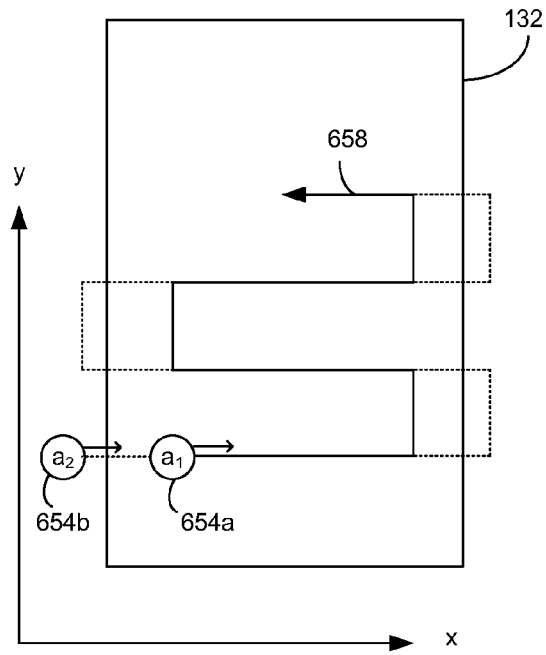
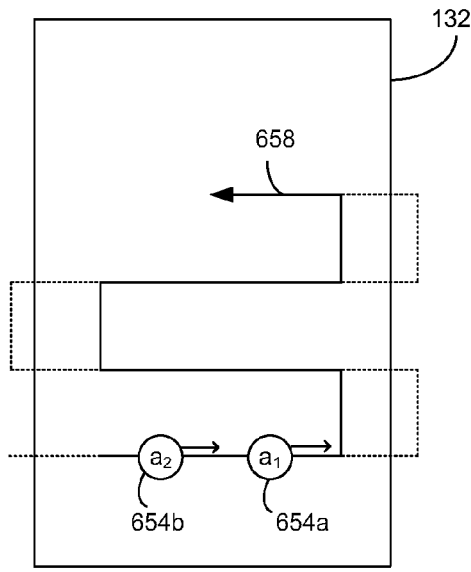
*Fig. 23A*      *Fig. 23B*
*Multi-Wavelength Scan on Sample*
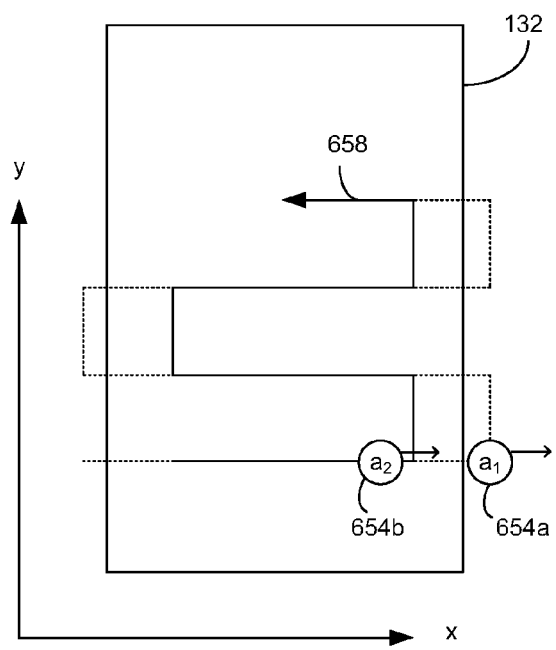
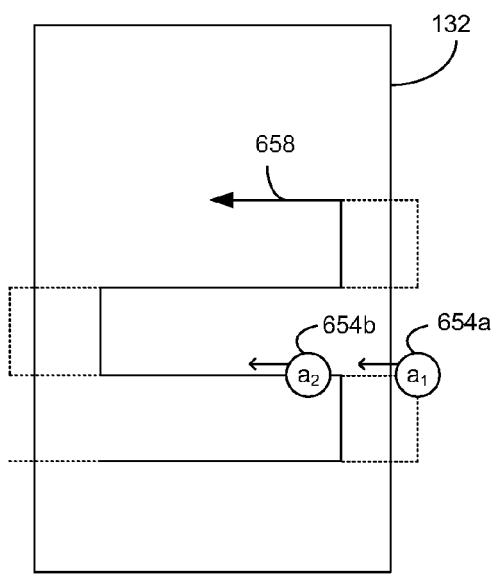
*Fig. 23C*      *Fig. 23D*

Multi-Wavelength Scan on Nondescanned Detector

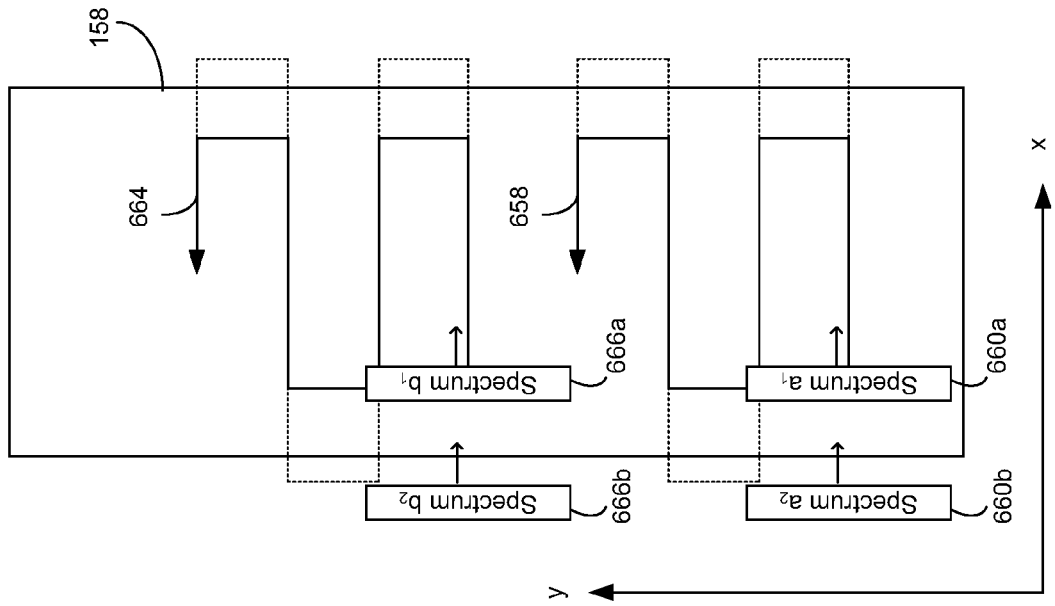
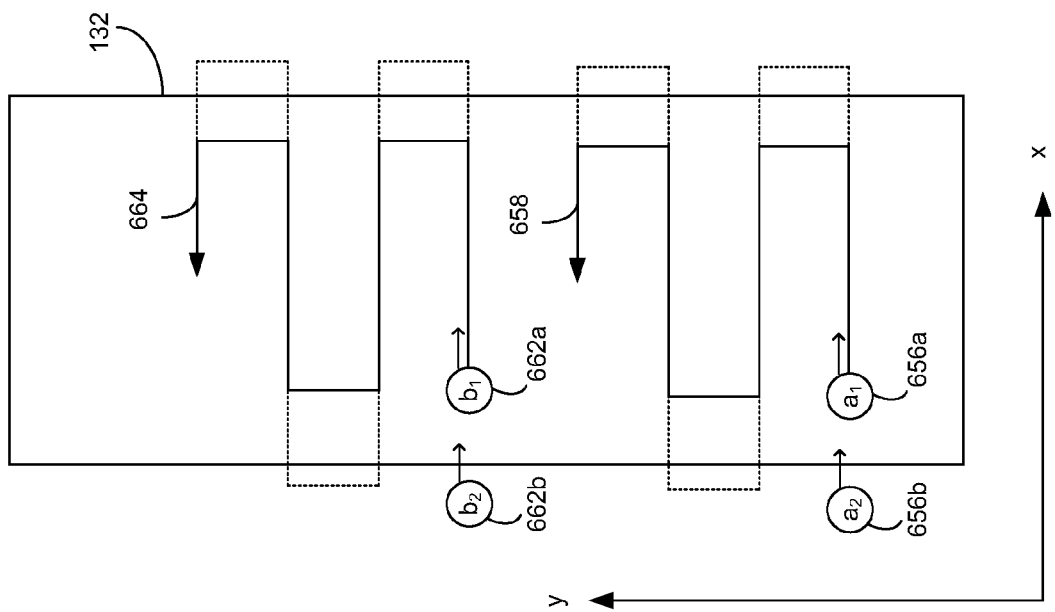
Fig. 25A
Fig. 25B

HIGH SPEED MICROSCOPE WITH SPECTRAL RESOLUTION

RELATED APPLICATIONS

The present application claims priority to U.S. Provisional Application 61/472,761, filed Apr. 7, 2011, and of U.S. Provisional Application 61/480,083, filed Apr. 28, 2011, the entire contents of each of which are hereby incorporated by reference.

BACKGROUND

Embodiments of the present invention relate to microscopes with spectral resolution.

SUMMARY

Laser scanning microscopes (such as two-photon and confocal microscopes) enable acquisition of images of narrow sections of cells and tissues that emit light in response to receiving laser energy. The images may include one or more spatial dimensions (e.g., x, y, and z dimensions). Multiple images may be stitched together or otherwise combined to create three-dimensional (3-D) images. In some instances, images are captured over a period of time to add a temporal dimension to the data collected. For example, images acquired over a period of time may be viewed in sequence to illustrate changes over time. In some instances, in addition to one or more spatial and temporal dimensions, a spectral dimension of the light emitted from the sample is obtained. Such spectral information provides various advantages, such as enabling the detection of fluorescence from multiple spectral variants of the samples' tags.

Embodiments of the present invention provide a system and method for high-speed microscopy with spectral resolution. Embodiments include a two-photon microscope with spectral resolution providing four- or five-dimensional fluorescence images of samples, including two or three spatial dimensions, a spectral dimension (for fluorescence emission), and a temporal dimension (on a scale from less than one second to about sixty seconds). Embodiments enable, via a single scan, generation of 2-D or 3-D (spatial) images for a complete wavelength spectrum.

High speed acquisition of spectrally resolved images of a sample enables the study of highly dynamic samples emitting energy (e.g., fluorescence, transmitted light, elastically scattered light (i.e., Raman scattered light), second and third harmonic generation, etc.) at multiple wavelengths of interest and a reduction in the time to study many samples in series. Furthermore, due to the speed with which photons can be collected and pixel data output by the camera, the laser power and, thereby, photon flux of the excitation beam, can be significantly increased. Additionally, providing a wide range of spectral resolution via a single scan for each sample voxel avoids the need for filter changes or multiple scans of the sample, which slow sample scanning times.

With the use of a combination of simultaneous multi-color analysis and rapid scanning methods detailed herein, the speed of analysis of a single slide can be reduced to a few minutes or less. In a research setting, the collection of data is accelerated and more rapid analysis on more samples can be performed. In turn, researchers are able to perform their work more rapidly and collect more data for statistical relevance. Embodiments of the invention enable cellular and molecular biologists, biochemists, and other life-scientists to investigate dynamic features of multiple protein populations, including co-localization and protein-complex formation and trafficking, and ligand-induced changes in conformation and oligomeric status.

In one embodiment, the invention provides a microscope for generating a multi-dimensional, spectrally resolved image. The microscope includes a light source that generates a pulsed light beam, a curved mirror that reflects the pulsed light beam as a light beam line, a scanning mechanism, a dispersive element, and a detector. The scanning mechanism scans the light beam line across a sample to cause the sample to emit energy. The dispersive element receives the emitted energy from the sample and disperses the emitted energy into spectral components that form continuous spectrum area, the continuous spectrum area corresponding to the light beam line. The detector receives the continuous spectrum.

Embodiments of the microscope further include a second curved mirror that reflects the pulsed light beam as a second light beam line. The scanning mechanism scans the second light beam line across the sample to cause the sample to emit additional energy. The dispersive element receives the additional emitted energy from the sample and disperses the additional energy into second spectral components that form a second continuous spectrum area, the second continuous spectrum area corresponding to the second light beam line. The detector receives the second continuous spectrum.

In another embodiment, the invention provides a multi-beam line scanning microscope for generating a multi-dimensional, spectrally resolved image. In this configuration, the microscope provides an acquisition speed higher than that of a single beam line scanning microscope by a factor equal to the number of lines, because each line of the multi-beam line scanning microscope scans a smaller area than the area scanned by a single line in a single line scanning microscope. The microscope includes a light source that generates a pulsed light beam, a multi-beam generator that receives the pulsed light beam and emits multiple light beams, a light beam line generator, a scanning mechanism, a dispersive element, and a detector. The light beam line generator receives the multiple light beams and emits multiple light beam lines. The scanning mechanism simultaneously scans the multiple light beam lines across a sample to cause the sample to emit energy. The dispersive element receives the emitted energy from the sample and disperses the emitted energy into spectral components that form continuous spectrum areas, each continuous spectrum area corresponding to one of the multiple light beam lines. The detector receives each continuous spectrum simultaneously.

In another embodiment, the invention provides a multi-beam point scanning microscope for generating a multi-dimensional, spectrally resolved image. The microscope includes a light source that generates pulsed light beam, a multi-beam generator that receives the pulsed light beam and emits multiple light beams, a scanning mechanism, a dispersive element, and a detector. The scanning mechanism simultaneously scans the multiple light beams across a sample, the sample emitting energy corresponding to each of the multiple light beams. The dispersive element receives the emitted energy from the sample and disperses the emitted energy into spectral components that form continuous spectrum lines, each continuous spectrum line corresponding to one of the multiple light beams. The detector receives each continuous spectrum line simultaneously.

In some embodiments, the multi-beam generator is one of a grating, a beam splitter, and an array of lenses. In some instances, the light beam line generator includes a first curved mirror and a second curved mirror, or a first lens and a second lens.

In some embodiments, the scanning mechanism includes computer-controlled x-y scanning mirrors positioned between the light source and the sample and/or computer-controlled sample positioners that move the sample to cause the multiple light beams to scan the sample. In some embodiments, the scanning mechanism further descans the energy emitted from the sample before the energy emitted from the sample reaches the detector, and the detector has a generally planar detection surface with a length and a width at least half the size of the length. The detector has a first axis along the length of the surface and corresponding to a spatial dimension of the sample, and a second axis along the width of the surface and corresponding to frequency.

In some embodiments, the microscope further includes an imaging module for receiving pixel data output by the detector and generating one or more images based on the pixel data. In some embodiments, the microscope is a two-photon microscope. Additionally, the curved mirror may be a deformable mirror shaped by control signals from a mirror controller. In some embodiments, the emitted energy is one of fluorescence, elastically scattered light, second harmonic signals, and third harmonic signals. In some embodiments, the microscope further includes a first and second objective. The first objective is positioned between the scanning mechanism and the sample, and receives the scanning light (e.g., light beam point(s) or light beam line(s)) from the scanning mechanism and transmits the scanning light to the sample. The second objective is positioned between the sample and the dispersive element, and receives the emitted energy from the sample and transmits the emitted energy to the dispersive element.

In some embodiments, the multiple light beams include at least a first light beam with a first wavelength, and a second light beam having a second wavelength. The first light beam and the second light beam follow the same path when scanned across the sample. Additionally, the first light beam and the second light beam alternate between leading and trailing positions along the path. The first light beam is scanned across the sample in an x-direction at a y-position, and the second light beam is simultaneously scanned across the sample in the x-direction at the y-position, the second light beam being offset in the x-direction from the first light beam. Additionally, the continuous spectrum line for the first light beam and the continuous spectrum line for the second light beam follow the same path across the detector during the scan. The continuous spectrum line for the first light beam and the continuous spectrum line for the second light beam alternate between leading and trailing positions along the path.

In another embodiment the invention provides a method of generating a multi-dimensional, spectrally resolved image. The method includes generating a pulsed light beam, reflecting, by a curved mirror, the pulsed light beam as a light beam line, a scanning step, a dispersing step, and a receiving step. In the scanning step, the light beam is scanned across a sample to cause the sample to emit energy. In the dispersing step, the emitted energy from the sample is dispersed into spectral components that form a continuous spectrum area, the continuous spectrum area corresponding to each point along the light beam line. In the receiving step, a detector receives the continuous spectrum.

The method may further include reflecting, via a second curved mirror, the pulsed light beam as a second light beam line; scanning the second light beam line across the sample to cause the sample to emit additional energy; dispersing the additional energy into second spectral components that form a second continuous spectrum area, the second continuous spectrum area corresponding to each point along second light beam line; and receiving, by the detector, the second continuous spectrum.

The method may also include outputting, by the detector, pixel data resulting from receiving the continuous spectrum and the second continuous spectrum. The pixel data is received by an imaging module. The imaging module then generates one or more images based on the pixel data.

In another embodiment, the invention provides a method of generating a multi-dimensional, spectrally resolved image. The method includes generating a pulsed light beam and receiving, via a multi-beam generator, the pulsed light beam. The multi-beam generator emits multiple light beams with round cross-sections in response to the pulsed light beam. The multiple light beams are focused by an objective to diffraction limited spots (or points) which are scanned across a sample, and the sample emits energy corresponding to each of the multiple light beams. The emitted energy is dispersed into spectral components that form continuous spectrum lines, with each continuous spectrum line corresponding to one of the multiple light beams. A detector receives each continuous spectrum line simultaneously.

In some embodiments, the detector outputs pixel data resulting from receiving the continuous spectrum lines, which is received by an imaging module. The imaging module then generates one or more images based on the pixel data.

Other aspects of the invention will become apparent by consideration of the detailed description and accompanying drawings.

BRIEF DESCRIPTION OF THE DRAWINGS

FIGS. 3A-B illustrate a multi-beam point scan on a sample and detector, respectively.

FIGS. 9A-E illustrate various shapes for curved mirrors used in embodiments of the invention.

FIGS. 10A-B illustrate a deformable mirror and associated controller.

FIGS. 11A-C illustrate various multi-beam generates used in embodiments of the invention.

FIG. 23A-D illustrates a sample receive excitation beams having various wavelengths.

FIG. 25A-B illustrates a sample and detector of a high speed microscope having pairs of excitation beams having various wavelengths.

DETAILED DESCRIPTION

Figure 1:
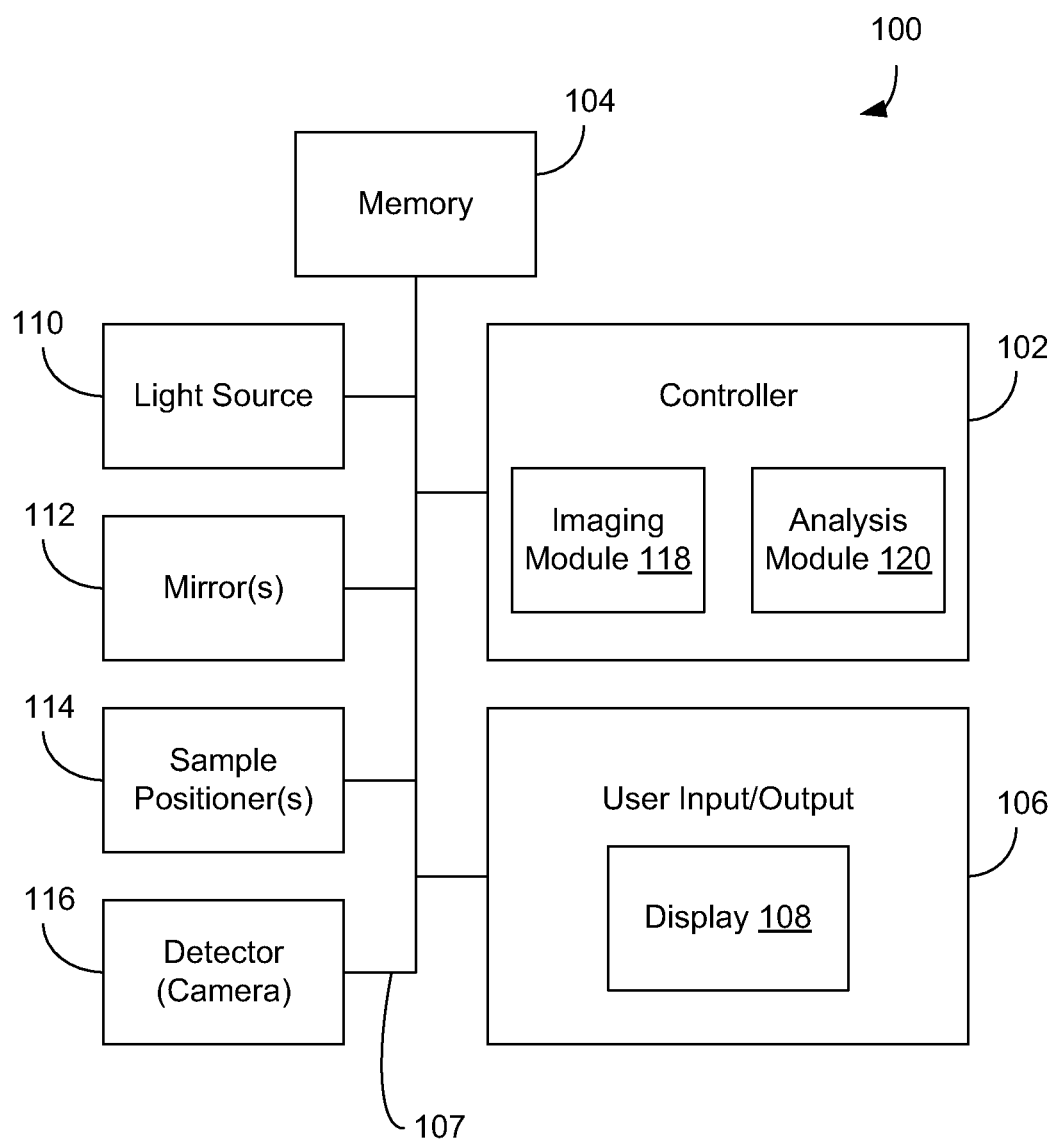
FIG. 1 illustrates a microscope system according to embodiments of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising," or "having" and variations thereof herein is meant to encompass the items listed thereafter and equivalents thereof as well as additional items. The terms "mounted," "connected," and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc.

It should be noted that a plurality of hardware and software based devices, as well as a plurality of different structural components may be utilized to implement the invention. Furthermore, and as described in subsequent paragraphs, the specific configurations illustrated in the drawings are intended to exemplify embodiments of the invention and that other alternative configurations are possible.

FIG. 1 illustrates a two-photon microscope system 100 including a controller 102, memory 104, and user input/output (I/O) 106 coupled together via bus 107. The controller 102 may include one or more of a general purpose processing unit, a digital signal processor, a field programmable gate array (FPGA), an application specific integrated circuit (ASIC), and other processing devices operable to carry out the functions attributable to the controller 102 and described herein. The memory 104 may store instructions executed by the controller 102 to carry out the aforementioned functions, may store data for the controller 102, such as image data, and may load data to the controller 102, such as program data, calibration data, etc. for use by the controller 102 during operation of the microscope system 100.

The user I/O 106 enables a user to interact with microscope system 100. For instance, the user I/O 106 includes a display 108 for displaying a graphical user interface to enable a user to control the microscope system 100 and to display images generated by the microscope system 100. The user I/O 106 may further include input devices (e.g., a mouse, keyboard, etc.) and, in some instances, the display 108 is a touch screen display capable of receiving user input. In some embodiments, the microscope system 100 further includes a communication module (not shown) for communicating with remote devices. For instance, the communication module may enable the microscope system 100 to communicate over a local area network (LAN), wide area network (WAN), the Internet, etc., via one or more of wired and wireless connections. Accordingly, images generated by the microscope system 100 may be shared with users on remote devices, stored on remote servers (e.g., on a "cloud"), sent to nearby portable devices (e.g., a smart phone, tablet, personal computer, laptop, etc.) of a local user.

The microscope system 100 further includes a light source 110, one or more mirror(s) 112, sample positioners 114, and a detector 116 (also referred to as a camera) in communication with the controller 102, memory 104, and user I/O 106 via bus 107. The controller 102 controls the light source 110 to generate light that is directed by the mirror(s) 112 towards a sample positioned by the sample positioners 114. The sample emits energy (e.g., light) towards the detector 116. The detector 116 may be, for instance, an electron multiplying charge coupled device that includes an array of pixels, a CMOS camera, a 2-D array of photomultiplier tubes, or another type of detector that includes a two-dimensional array of pixels. The detector outputs a digital signal or signals (i.e., pixel data) to the controller 102 representative of the intensity of light from the sample that impinges the array of pixels. The controller 102 includes an imaging module 118 that interprets the data from the detector 116 and forms an image of the array of the sample being investigated. The controller 102 further includes an analysis module 120 for analyzing the pixel data from the detector 116 and/or images formed by the imaging module 118.

Figure 2:
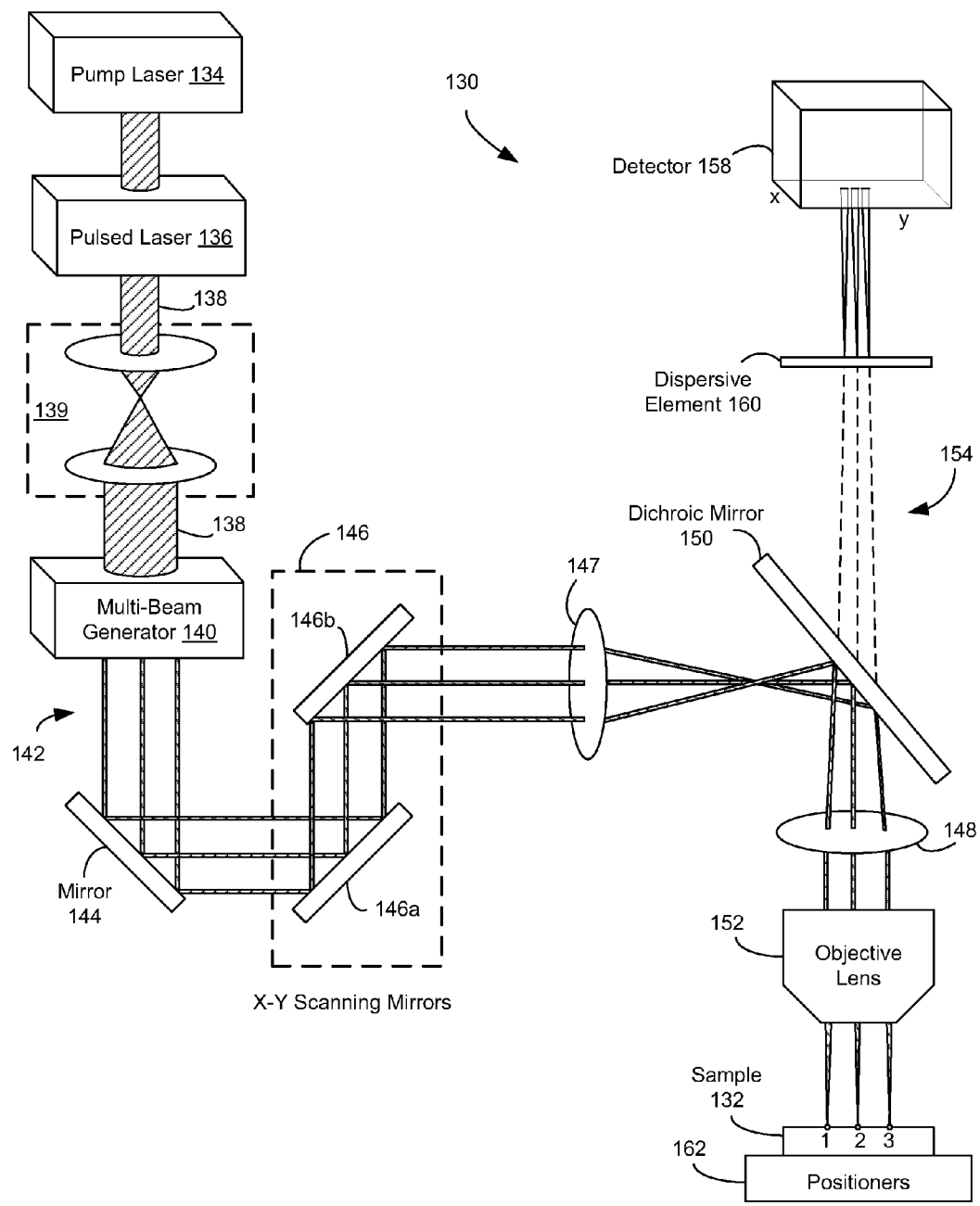
FIG. 2 illustrates a multi-beam point scanning microscope with spectral resolution.

FIG. 2 illustrates the microscope system 100 implemented as a multi-beam point scanning microscope 130 for analyzing sample 132. For simplification, the controller 102, memory 104, user I/O 106, and bus 107 are not shown. The microscope 130 includes a pump laser 134 and a pulsed laser 136 for emitting a pulsed beam of light 138 towards a telescope 139. The telescope 139 expands and transmits the pulsed beam of light 138 towards a multi-beam generator 140. The pump laser 134 may be a high power solid state laser operating at five watts to provide continuous wave (CW) light at a wavelength of 532 nanometers (nm), although other pump lasers 134 and other laser outputs may be used in some embodiments. The pulsed laser 136 may be a mode-locked TI:Sapphire laser that generates femtosecond pulses of near-infrared light (centered at approximately 800 nm with a bandwidth of a few nm to 120 nm). In some embodiments, the pulsed laser 135 is a different laser type and/or generates light having a different wavelength and bandwidth. In some embodiments, light generating devices different from the pump laser 134 and pulsed laser 136 are used to generate light for the microscope 130.

The multi-beam generator 140 converts the pulsed beam of light 138 into multiple beams 142. In FIG. 2, the multi-beam generator 138 is shown to generate three beams 142. Generally, the multiple beams 142 are formed to be substantially equivalent (e.g., in intensity, wavelength, etc.). Exemplary multi-beam generators 138 are described in greater detail with respect to FIG. 11A-C. The multiple beams 142 are reflected by the mirror 144 towards a pair of computer-controlled x-y scanning mirrors ("scanning mirrors") 146, including mirrors 146a and 146b. The "x" and "y" of the x-y scanning mirrors refer to orthogonal directions on the sample 132. In some embodiments, the scanning mirrors 146 are a pair of mirrors attached to galvanometric scanners having a 10 mm aperture.

The multiple beams 142 reflected by the scanning mirrors 146 are received by a lens 147. The lens 147 focuses and transmits the multiple beams 142 to a dichroic mirror 150. The dichroic mirror 150 is a short pass mirror that reflects light having a long wavelength, but allows light having a short wavelength to pass through. Accordingly, the long wavelength portions of the multiple beams 142 transmitted from the lens 147 are reflected towards lens 148. In some embodiments, a long pass mirror that reflects light having a short wavelength, but allows light having a long wavelength to pass through. The lens 148 collimates and transmits the light beams 142 to an objective lens 152. The objective lens 152 focuses each point of the multiple beams 142 to a unique diffraction-limited spot (i.e., point) of the sample 132. The spots are generally at the same x-dimension location on the sample 132, but spaced apart in the y-dimension. Using diffraction limited beam points (spots) helps avoid photo bleaching of areas of the sample not being scanned at that moment.

As each of the diffraction limited spots is scanned across the sample 132 in the x-direction by the scanning mirrors 146, the sample emits fluorescence beams 154 back to the objective lens 152. The fluorescence beams 154 are transmitted by the objective lens 152 to the lens 148. The lens 148 focuses each of the emitted fluorescence beams 154 to a particular point on an electron multiplying charge-coupled device (detector) 158. The fluorescence beams 154, however, first pass through the short-pass dichroic mirror 150 and a light dispersive element 160. The short-pass dichroic mirror 150 allows visible light to pass through, while reflecting most of the infrared light components of the emitted fluorescence beams 154. The dispersive element 160 disperses the light into its spectral components to form a continuous spectrum of varying wavelengths that spread in the y-direction of the detector 158. Accordingly, the fluorescence beams 154, after passing through the dispersive element 160, reach the detector 158 as three wavelength spectra extending along the y-direction. Each wavelength spectrum impinges the detector 158 at the same x-position, but is spaced apart in the y-direction.

In some instances, an additional short pass filter (not shown) is provided between the dichroic mirror 150 and the dispersive element 160 to further eliminate residual infrared components of the emitted fluorescence beams 154 not filtered by the dichroic mirror 150, which could otherwise overwhelm the visible components of interest on the detector 158.

In the above embodiments, the sample 132 is assumed to be positioned on a static platform while the impinging light is scanned. In some embodiments, rather than scanning the multiple beams 142 across the sample 132 using scanning mirrors 146, sample positioners 162 (e.g., nanopositioners) are used to move the sample while the scanners 132 and, therefore, the multiple beams 142, remain in a static position. In some embodiments, to perform a complete area scan of the sample 132, the scanning mirrors 146 scan the multiple beams 142 in a single direction (e.g., the x- or y-direction), while the sample positioners 162 are used to move the sample in the other direction (e.g., the other of the x- or y-direction). The sample positioners 162 and the static platform stand may both be referred to as a sample holder. Furthermore, the sample holder may include an automatic loading system to enable the scanning of a plurality of samples, one after another. For instance, the sample holder may include an automatic slide changer that is loaded with samples 132 and that moves the samples, one after another, into position for scanning the samples serially.

FIG. 3A illustrates a multi-beam point scan on the sample 132 using the microscope 130. FIG. 3A depicts the beam points 142a-c in their respective starting positions at the beginning of a scan. The beam points 142a-c are spaced apart in the y-direction on the sample 132. The beam points 142a-c, synchronously follow their respective scan paths 170a-c. The scan paths 170a-c sweep across the sample 132 in the x-direction, increment in the y-direction, sweep back across in the x-direction, and so on, until the scan completes. A single scan of the sample 132 is completed when each portion in the scan area of the sample 132 has been impinged by one of the beam points 142a-c. Accordingly, the single scan is complete when the beam point 142a reaches the start position of the beam point 142b, the beam point 142b reaches the start position of the beam point 142c, and the beam point 142c reaches the end of the scan area, which generally occur simultaneously.

FIG. 3B illustrates the resulting emitted fluorescence beams 154a-c on the detector 158. As noted above, the emitted fluorescence beams 154 pass through a dispersive element 160 causing each point to be dispersed into its spectral components forming spectra 172a-c on the detector, one for each emitted fluorescence beam 154a-c. The spectra 172a-c have a line shape extending along the y-direction, and each is positioned at the same x-position and spaced apart in the y-direction. Each spectrum 172 is formed of a continuous spread of the emitted fluorescence over a range of wavelengths. Each point along the y-axis of the spectrum 172 includes components of the emitted fluorescence at a different wavelength. For instance, the upper/top portion of the spectrum 172 may include the larger wavelengths components, while the lower/bottom portion includes the shorter wavelength components. The spectrum 172 is a continuous spectrum. The spectra 172a-c generally follow the same paths 170a-c as their corresponding beam points 142a-c. Pixel data is obtained from the detector 158 as the spectra 172a-c reach each point along the scan paths 170a-c, which corresponds to the beam points 142a-c reaching each positions of the sample 132 along scan path 170a-c.

In a single beam point scan implementation, only a single beam point (e.g., 142a) is generated and only a single spectrum (e.g., 172a) results on a detector. Accordingly, the path 170 of the single beam point and single spectrum traverses the entire sample area. In contrast, in the multi-beam scanning microscope 130, the sample area is more quickly scanned because, rather than a single beam point, three beam points 142a-c cover the same area. Assuming three beam points 142a-c, the time for the multi-beam scanning microscope 130 to scan the sample 132 is effectively performed in one-third the time of a single beam point scan. Accordingly, assuming a 10 to 60 second scan for a single beam point scan, a multi-beam scanning microscope 130 with three beam points would reduce the scan time to between approximately 3 to 20 seconds. The number of beam points may be reduced to two or increased beyond three. However, the beam points 142 should remain spaced apart enough such that the resulting spectra 172 do not overlap on the detector in the y-direction.

Figure 4:
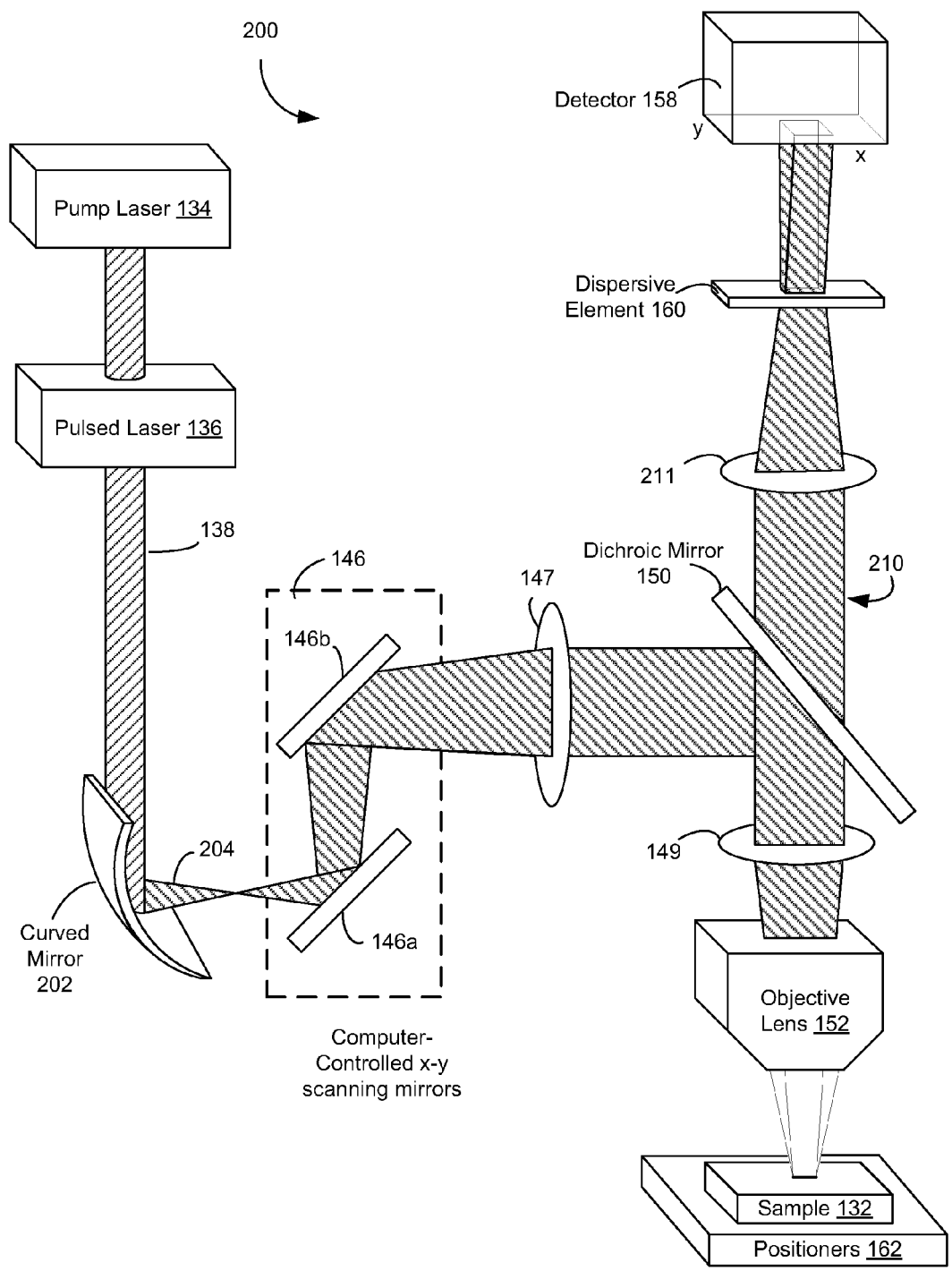
FIG. 4 illustrates a single-beam line scanning microscope with spectral resolution.

FIG. 4 illustrates the microscope system 100 implemented as a single beam line scanning microscope 200 for analyzing sample 132. For simplification, the controller 102, memory 104, user I/O 106, and bus 107 of FIG. 1 are not shown. In FIG. 4, elements similar to those of FIG. 2 are similarly numbered and perform similar functions, unless otherwise noted or necessitated by differences in the respective microscopes. In contrast to multi-beam point scanning microscope 130, single beam line scanning microscope 200 includes a curved mirror 202 and does not include a multi-beam generator 140. Accordingly, the beam 138 emitted from the pulsed laser 136 is received by the curved mirror 202, which reflects the beam 138 as a beam line 204.

Figure 5:
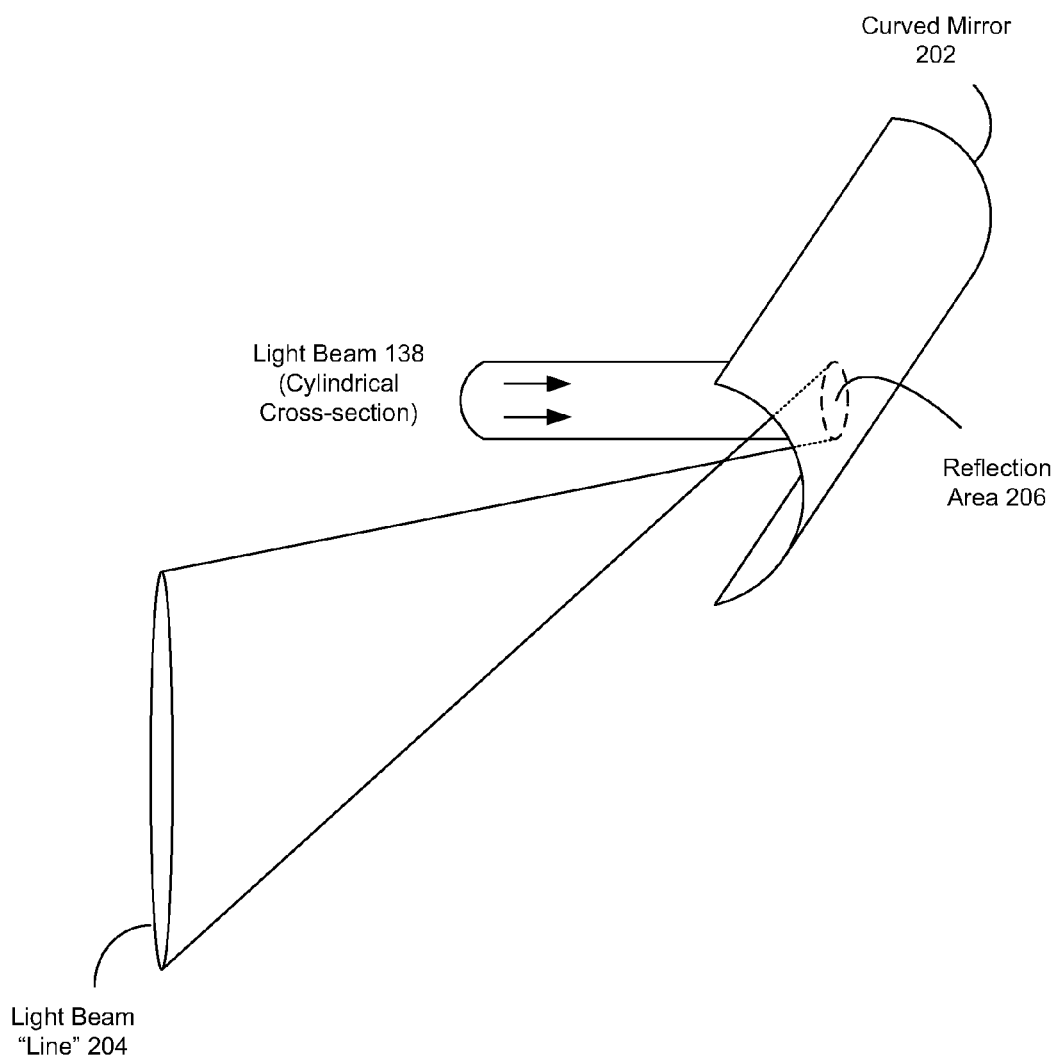
FIG. 5 illustrates a curved mirror generating a beam line.

FIG. 5 illustrates how the curved mirror 202 reflects a beam of light as a line. As shown in FIG. 5, the light beam 138 having a generally circular or cylindrical cross section is received by the curved mirror 202 at a reflection area 206. The reflection of the light beam 138 is "stretched" such that an elongated oval is formed. The oval retains substantially the same cross-sectional width as the light beam 138, but the length is increased such that the reflection has, effectively, a line shape. While other devices are capable of converting a beam 138 into a beam line 204, the curved mirror 202 provides certain advantages. For example, a cylindrical lens may be used to convert the beam 138 into the beam line 204; however, the lens produces a line with lower axial resolution. For instance, the lens includes certain chromatic aberrations that reduce the axial resolution.

Returning to FIG. 4, the beam line 204 is reflected towards the x-y scanning mirrors 146, which reflect the beam line 204 towards a lens 147. As described below with respect to FIG. 6A, the beam line 204 is scanned in the y-direction on the sample, but not the x-direction. Accordingly, one of the x-y scanning mirrors may remain stationary during a beam line scan of the sample. The lens 147 collimates the beam line 204 and transmits the beam line 204 to the dichroic mirror 150. The dichroic mirror 150 reflects the beam line 204 to the lens 149, which, along with the objective lens 152, focuses the beam line 204 on the sample 132 as a diffraction-limited line. The diffraction-limited line is scanned across the sample 132 in the y-direction by the scanning mirrors 146, and the sample 132 emits a fluorescence beam line 210 back to the objective lens 152 and lens 149. The objective lens 152 may be an infinity-corrected high numerical aperture objective, an F-Theta lens, or another focusing device. F-Theta lenses are designed to provide a flat field at the image plane of the scanning system, which is particularly beneficial for line scanning.

The fluorescence is transmitted by the lens 149 through the short-pass dichroic mirror 150 and through the lens 211 (e.g., a tube lens). The lens 211 focuses the fluorescence beam line 210 to a line on the detector 158. Before reaching the detector 158, however, the emitted fluorescence beam line 210 passes through the light dispersive element 160. The dispersive element 160 disperses the fluorescence beam line 210 into its spectral components to form a continuous spectrum of varying wavelengths that spread in the y-direction of the detector 158. Accordingly, the fluorescence beam line 210, after passing through the dispersive element 160, reaches the detector 158 as an area with wavelength spectra extending along the y-direction and the x-dimension of the area corresponding to the x-dimension of the sample 132.

Figure 6:
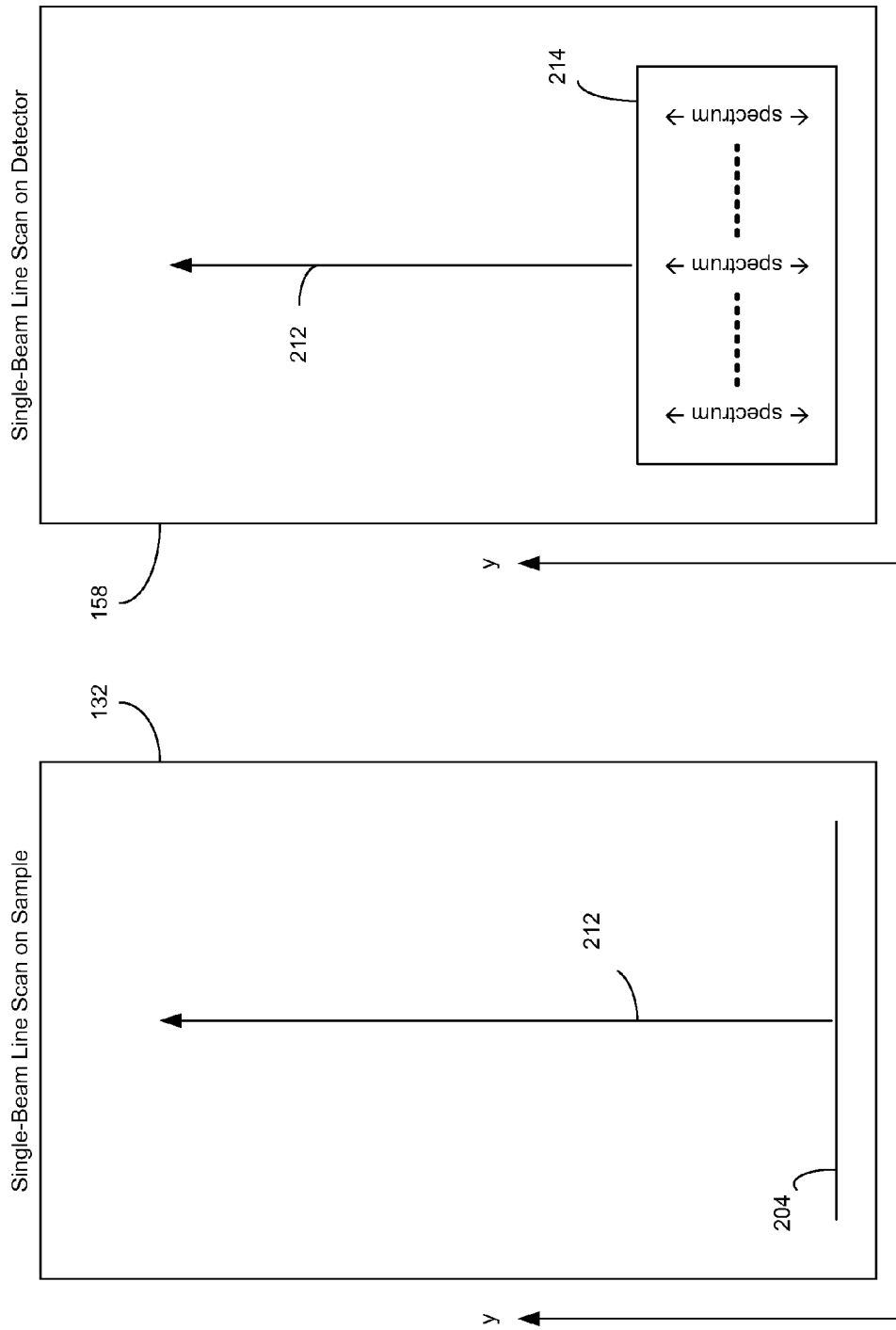
FIGS. 6A-B illustrate a single-beam line scan on a sample and detector, respectively.

FIG. 6A illustrates a single-beam line scan on the sample 132 using the microscope 200. FIG. 6A depicts the beam line 204 in its starting position at the beginning of a scan. During a scan, the beam line 204 moves in the y-direction along the scan path 212. A single scan is complete when the beam line 204 reaches the uppermost desired y-position of the sample 132 along the scan path 212.

FIG. 6B illustrates the resulting emitted fluorescence beam line 210 on the detector 158. The area spectrum 214 generally follows the same path 212 as the corresponding beam line 204. As noted above, the emitted fluorescence beam line 210 passes through a dispersive element 160 causing the beam line 210 to be dispersed into its spectral components forming an area spectrum 214 on the detector 158. The area spectrum 214 has a rectangular shape extending along the x- and y-direction. The y-direction corresponds to wavelength, and the x-direction corresponds with the spatial, x-dimension of the sample 132. Accordingly, each point along the x-direction of the area spectrum 214 has a continuous spread of the emitted fluorescence over a range of wavelengths in the y-direction of the detector 158. The area spectrum 214 is associated with the (spatial) y-position of the sample 132 currently receiving the beam line 204. Pixel data is obtained from the detector 158 as the area spectrum 214 reaches each y-position, which corresponds to the beam line 204 reaching each y-positions of the sample 132 along scan path 212.

In the single-beam line scan implementation, the scan speed is improved relative to a single beam point scan in that the line covers the x-dimension of the sample 132 to be scanned, and the beam line 204 is merely moved along the y-dimension of the sample 132. As such, each point along the x-dimension of the sample 132 is excited simultaneously by the beam line 204. In a single-beam line scan implementation, the speed of the detector 152 may become the limiting factor for the time to complete a scan. That is, the scan will be as fast as the detector 158 can convert received fluorescence and export corresponding pixel data, which, with current technology, results in a scan time of a sample being under 10 seconds. The scan time may be further improved with faster detector technology.

Figure 7:
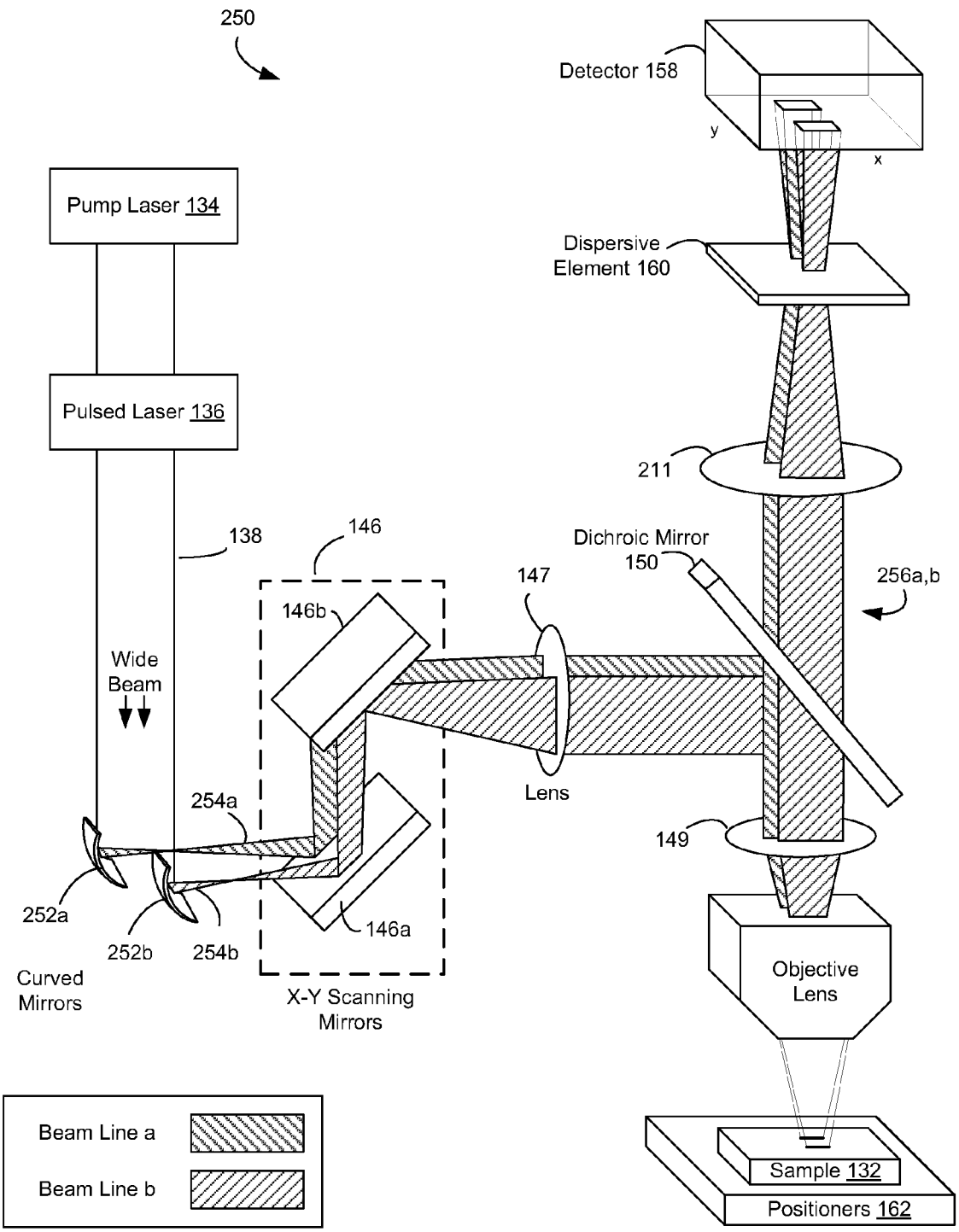
FIG. 7 illustrates a multi-beam line scanning microscope with spectral resolution.

FIG. 7 illustrates the microscope system 100 implemented as a multi-beam line scanning microscope 250 for analyzing sample 132. For simplification, the controller 102, memory 104, user I/O 106, and bus 107 of FIG. 1 are not shown. In FIG. 7, elements similar to those of FIGS. 2 and 4 are similarly numbered and perform similar functions, unless otherwise noted or necessitated by differences in the respective microscopes.

In the multi-beam line scanning microscope 250, the beam 138 emitted from the pulsed laser 136 is received by two curved mirrors 252a and 252b, which reflect the beam 138 as a beam lines 254a and 254b, respectively. The beam lines 254a-b are reflected towards the x-y scanning mirrors 146, which reflect the beam lines 254a-b towards the lens 147. The lens 147 collimates the beam lines 254a-b and transmits the beam lines 254a-b to the dichroic mirror 150. The dichroic mirror 150 reflects the beam lines 254a-b to the lens 149 and the objective lens 152, which focus the beam lines 254a-b on the sample 132 as diffraction limited lines. The diffraction limited lines are parallel with each other along the x-dimension of the sample 132 and spaced apart in the y-dimension of the sample. The diffraction limited lines are scanned across the sample 132 in the y-direction by the scanning mirrors 146, and the sample 132 emits fluorescence beam lines 256a-b back to the objective lens 152 and lens 149. The emitted fluorescence beam lines 256a and 256b correspond to the beam lines 254a and 254b, respectively. The objective lens 152 may be an infinity-corrected high numerical aperture objective, an F-Theta lens, or another focusing device. As noted above, the F-Theta lens is particularly beneficial for line scanning.

The fluorescence is transmitted by the objective lens 152 and lens 149 through the short-pass dichroic mirror 150 and through the lens 211. The lens 211 focuses the fluorescence beam lines 256a-b to corresponding lines on the detector 158. Before reaching the detector 158, however, the emitted fluorescence beam lines 256a-b pass through the light dispersive element 160. The dispersive element 160 disperses the fluorescence beam lines 256a-b into their spectral components to form a continuous spectrum of varying wavelengths that spread in the y-direction of the detector 158. Accordingly, the fluorescence beam lines 256a-b, after passing through the dispersive element 160, reach the detector 158 as areas with wavelength spectra extending along the y-direction and the x-direction corresponding to the x-dimension of the sample 132.

Figures 8A, 8B:
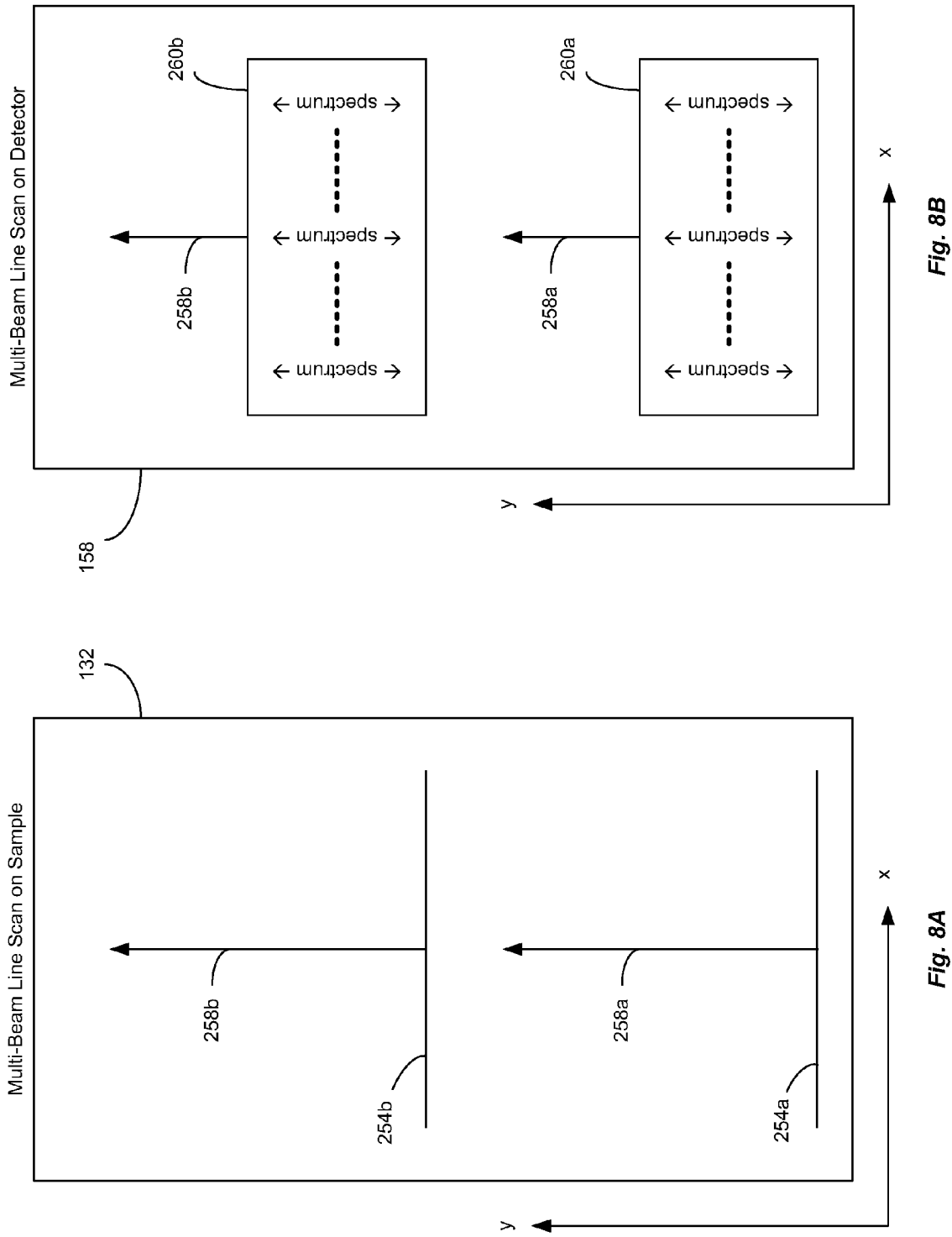
FIGS. 8A-B illustrate a multi-beam line scan on a sample and detector, respectively.

FIG. 8A illustrates a multi-beam line scan on the sample 132 using the microscope 250. FIG. 8A depicts the beam lines 254*a-b* in their respective starting position at the beginning of a scan. During a scan, the beam lines 254*a-b* move in the y-direction along the scan paths 258*a-b*, respectively.

FIG. 8B illustrates the resulting emitted fluorescence beam lines 254*a-b* on the detector 158. The area spectra 260*a-b* generally follow the same paths 258*a-b* as the corresponding beam lines 254*a-b*. As noted above, the emitted fluorescence beam lines 256*a-b* pass through a dispersive element 160 the beam lines 256*a-b* to be dispersed into its spectral components forming area spectra 260*a-b* on the detector 158. The area spectra 260*a-b* have rectangular shapes extending along the x- and y-direction. The y-direction corresponds to wavelength, and the x-direction corresponds with the spatial, x-dimension of the sample 132. Accordingly, each point along the x-direction of the area spectra 260*a-b* has a continuous spread of the emitted fluorescence over a range of wavelengths in the y-direction of the detector 158. Pixel data is obtained from the detector 158 as the area spectra 260*a-b* reach each y-position, which corresponds to the beam lines 256*a-b* reaching each y-positions of the sample 132 along scan path 258*a-b*.

In the multi-beam line scan implementation, the scan speed is improved relative to a single and multi-beam point scans in that the lines 254*a* and 254*b* cover the x-dimension of the sample 132 to be scanned. That is, each point along the x-dimension of the sample 132 at a first y-position is scanned simultaneously by the beam line 254*a*, and each point along the x-dimension of the sample 132 at a second y-position is scanned simultaneously by the beam line 254*b*. To complete a single scan, the beam lines 254*a-b* are merely moved along the y-dimension of the sample 132 along paths 258*a-b*.

In the multi-beam line scan implementation, the scan speed is improved relative to a single beam line scan in that two beam lines 256*a* and 256*b* simultaneously cover different regions of the sample 132, which are offset along the y-dimension of the sample. See, for example, FIGS. 8A-B compared with FIGS. 6A-B. As the microscope 250 includes two beam lines 254*a* and 254*b*, a scan of the sample 132 is approximately twice as fast as a scan with a single beam line (e.g., via microscope 200 of FIG. 4). Accordingly, similar to a single-beam line scan implementation, the speed of the detector 152 may become the limiting factor for the time to complete a scan.

Although the microscope 250 is shown in FIG. 7 with two curved mirrors 252 each generating a beam lines 254, in some embodiments, additional curved mirrors 252 are provided to generate additional beam lines 254. The additional beam lines 254 are used to further increase the speed of a scan of a sample 132. In general, the areas 260 resulting from the multiple beam lines 254 should not overlap in the y-direction on the detector 158.

In some embodiments, the multi-beam line microscope 250 generates multiple beam lines 256 using alternative techniques. For example, in some embodiments, the microscope 250 includes a multi-beam generator, similar to the multi-beam generator 140. The multi-beam generator is positioned to receive the light 138 and emit multiple beams. One or more curved mirror(s) 252 receive the beams emitted from the multi-beam generator and the curved mirror(s) 252 reflect each received beam to generate corresponding beam lines 254.

The curved mirrors 252 may also be referred to as beam line generators. In some embodiments, curved mirrors 252 are replaced with other beam line generators. For instance, the beam line generators may include one or more lenses to receive the wide beam 138 and generate multiple beam lines, or to receive multiple beams from the multi-beam generator 140 and generate multiple beam lines.

The curved mirrors 208 and 252 may have various shapes. For example, FIGS. 9A-E illustrate cross-sections of curved mirrors 208 and 252 having various shapes. FIG. 9A-C illustrates the curved mirrors 208 and 252 as a circularly curved mirror 280, an elliptical mirror 282, and a parabolic mirror 284, respectively. FIG. 9D illustrates the curved mirrors 208 and 252 as a curved mirror 286 having a non-uniform curve. A light wave front is generally not smooth or uniform. Rather, the light wave front includes aberrations that, cause, for instance, the light to not land directly on a surface as desired. The imperfections in the curve of the curved mirror 286 help compensate for the aberrations of a light wave front. FIG. 9E illustrates the curved mirrors 252 as a mirror unit 288 having multiple mirror curves 288*a-e*. The mirror unit 288 may be a single, integrated unit made of a continuous material. In some instances, the mirror unit 288 includes individual curved mirrors (i.e., 288*a-e*) mechanically coupled together to form an array, or may consist of a single deformable mirror in which individual actuators are configured such that the whole deformable mirror surface resembles a cylindrical mirror or an array of smaller mirrors.

FIGS. 10A-B illustrate a controlled deformable mirror 290 coupled to a mirror controller 292, which may be used to implement the curved mirrors 208 and 252. The deformable mirror 290 includes an array of reflective surfaces 294 on top of actuators 296. The actuators 296 are controlled by the output signals from the mirror controller 292 to adjust the shape of the deformable mirror 290. For example, in FIG. 10A, the controller 292 outputs signals to the actuators 296 to control the deformable mirror 290 to have a flat, planar shape. In contrast, in FIG. 10B, the mirror controller 292 controls the actuators 296 to control the deformable mirror 290 to have a curved shape. The deformable mirror 290 may be controlled to have any of the shapes in FIGS. 9A-E, as well as other shapes. Accordingly, the deformable mirror 290 may be selectively controlled to alter the scanning of a microscope system. For instance, in the microscope 200, the deformable mirror 290 may be controlled to be the curved mirror 202 to perform a beam line scan. Additionally, the deformable mirror 290 may be controlled to be a flat mirror to cause the microscope 200 to perform a beam point scan (see, e.g., FIGS. 1 and 2), or to be a series of curved mirrors to cause the microscope to perform multi-beam line scanning (e.g., FIG. 7).

In some embodiments, the mirror controller 292 is further coupled to a light sensor 298 for detecting the incident light reflected by the deformable mirror 290. The light sensor 298 provides feedback to the controller 292 to more precisely control the deformable mirror 290 to produce the desired light reflections. For instance, the deformable mirror 290 may be controlled to produce a non-uniform mirror such as illustrated in FIG. 9D. The feedback from the light sensor 298 enables the mirror controller 292 to adjust the deformable mirror 290 to produce a desired reflection that compensates for aberrations in the light wave 299.

FIGS. 11A-C illustrates various multi-beam generators that may be used to implement multi-beam generator 140. FIG. 11A illustrates a multi-beam generator 300 including a beam splitter 302 and mirror 304. The multi-beam generator 300 receives a light beam 306*a* from a light source 308. The light beam 306*a*, with initial power (P), is transmitted to the multi-beam generator 300. The light beam 306*a* is received and reflected by the mirror 304. The beam splitter 302 receives the reflected light beam 306a and reflects a light beam 306b having power (P)=0.9·P. The remaining 10% of P of the light beam 306a passes through the beam splitter 302 as light beam 310a. The light beam 306b is received and reflected by the mirror 304. The beam splitter 302 receives the reflected light beam 306b and reflects a light beam 306c having P=0.8·P. The remaining 10% of P of the light beam 306b passes through the beam splitter 302 as light beam 310b. The light beam 306c is received and reflected by the mirror 304. The beam splitter 302 receives the reflected light beam 306c and reflects a light beam 306d having P=0.7·P. The remaining 10% of P of the light beam 306c passes through the beam splitter 302 as light beam 310c. Accordingly, the multi-beam generator 300 receives a single light beam with power P, and outputs three light beams each having power 10% of P. The multi-beam generator 300 may have the mirror 304 and beam splitter 302 extended further to produce additional light beams or reduced to produce fewer beams.

FIG. 11B illustrates a multi-beam generator 320 having an array of lenses 322 receiving a single, wide light beam 324. Each lens 322 focuses a portion of the wide light beam 324 to a point 326a-e. In some embodiments, more or fewer lenses 322 are provided to alter the number of beam points generated by the multi-beam generator 320.

FIG. 11C illustrates a multi-beam generator 330 having an optical grating 332 that receives a single light beam 334. The optical grating 332 is a diffractive element designed to produce five light beams 336a-e of approximately equal intensities. In some embodiments, the optical grating 332 is designed to produce more or fewer light beams 336a. In other embodiments, the multi-beam generator 330 includes a diffractive element formed of one or more prisms, a spatial light modulator, or another device that can produce multiple beams through a process of diffraction.

The microscopes 130, 200, and 250 are described and illustrated above as non-descanned microscopes. In non-descanned microscopes, the fluorescence emitted from a sample does not pass back through the x-y scanning mirrors. Rather, the fluorescence proceeds to the detector 158 without being "descanned" by scanning mirrors. Accordingly, the emitted fluorescence is scanned across the detector 158 following essentially the same path as the light beams scanning the sample. See, for example, FIGS. 3A-B, 6A-B, and 8A-B.

In a descanned microscope, the fluorescence emitted from the sample passes back through the x-y scanning mirrors before reaching the camera. Accordingly, the emitted fluorescence remains stationary on the camera. For image reconstruction, the positions of the x-y scanning mirrors are monitored such that the microscope system is able to associate emitted fluorescence with particular locations of the sample being scanned. In a half-descanned microscope (also referred to as half non-descanned microscope), the emitted fluorescence passes through one of the x-y scanning mirrors, but not both. Accordingly, the emitted fluorescence is static in one of the x-dimension and y-dimension on the camera, but is scanned across the camera in the other of the x-dimension and y-dimension.

Figure 12:
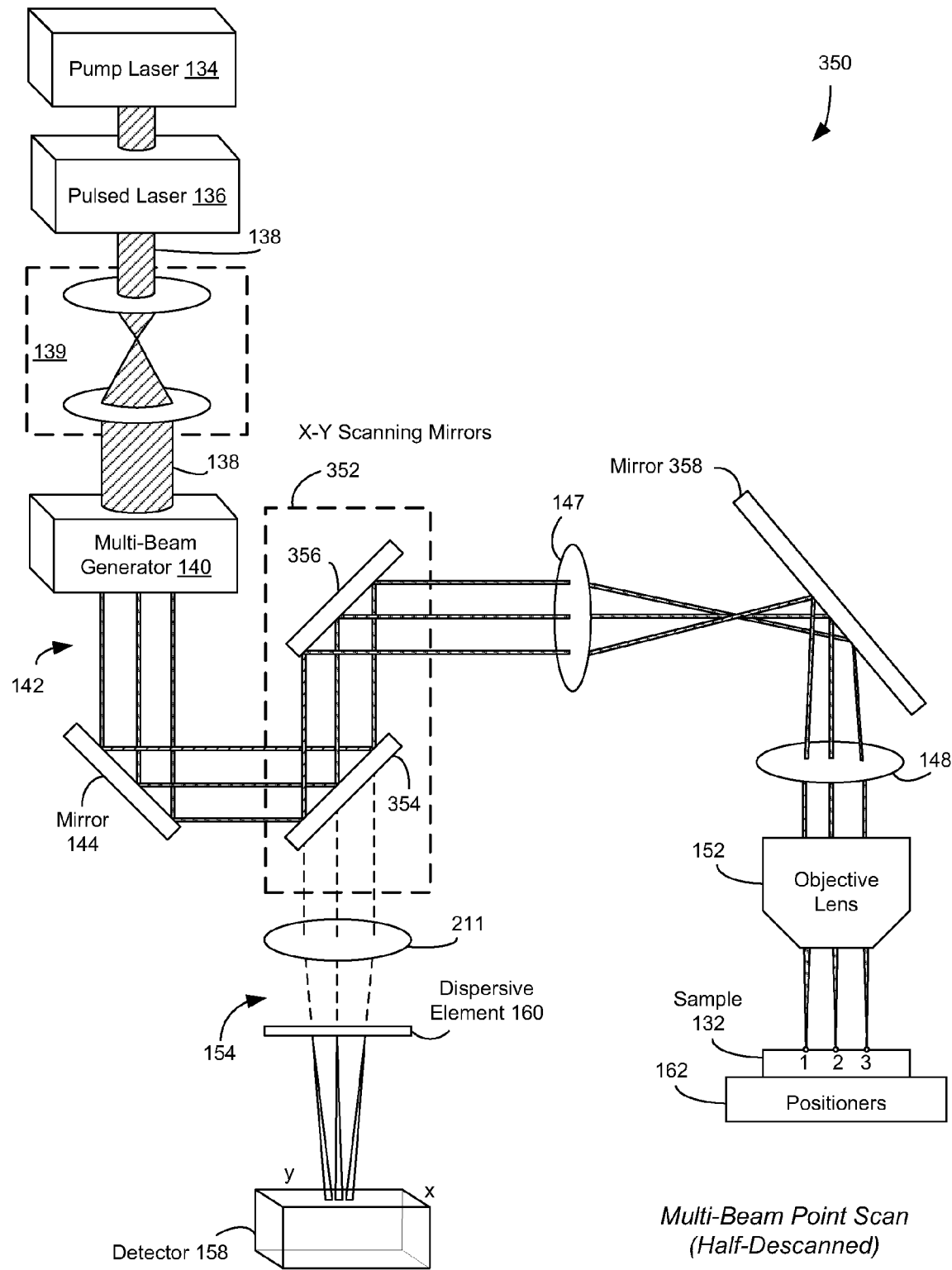
FIG. 12 illustrates a half-descanned, multi-beam point scanning microscope with spectral resolution.
Figure 13:
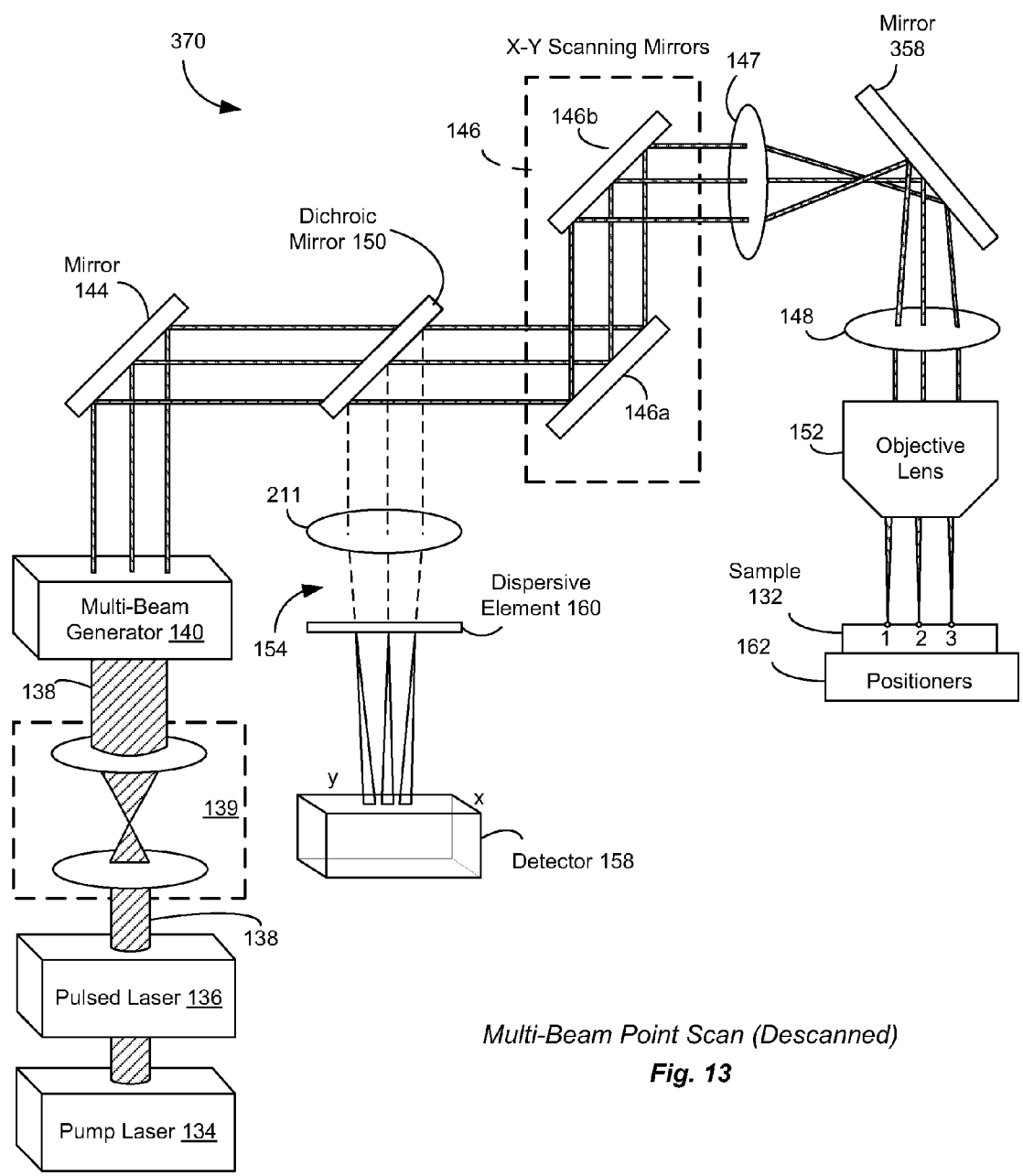
FIG. 13 illustrates a descanned, multi-beam point scanning microscope with spectral resolution.
Figure 14:
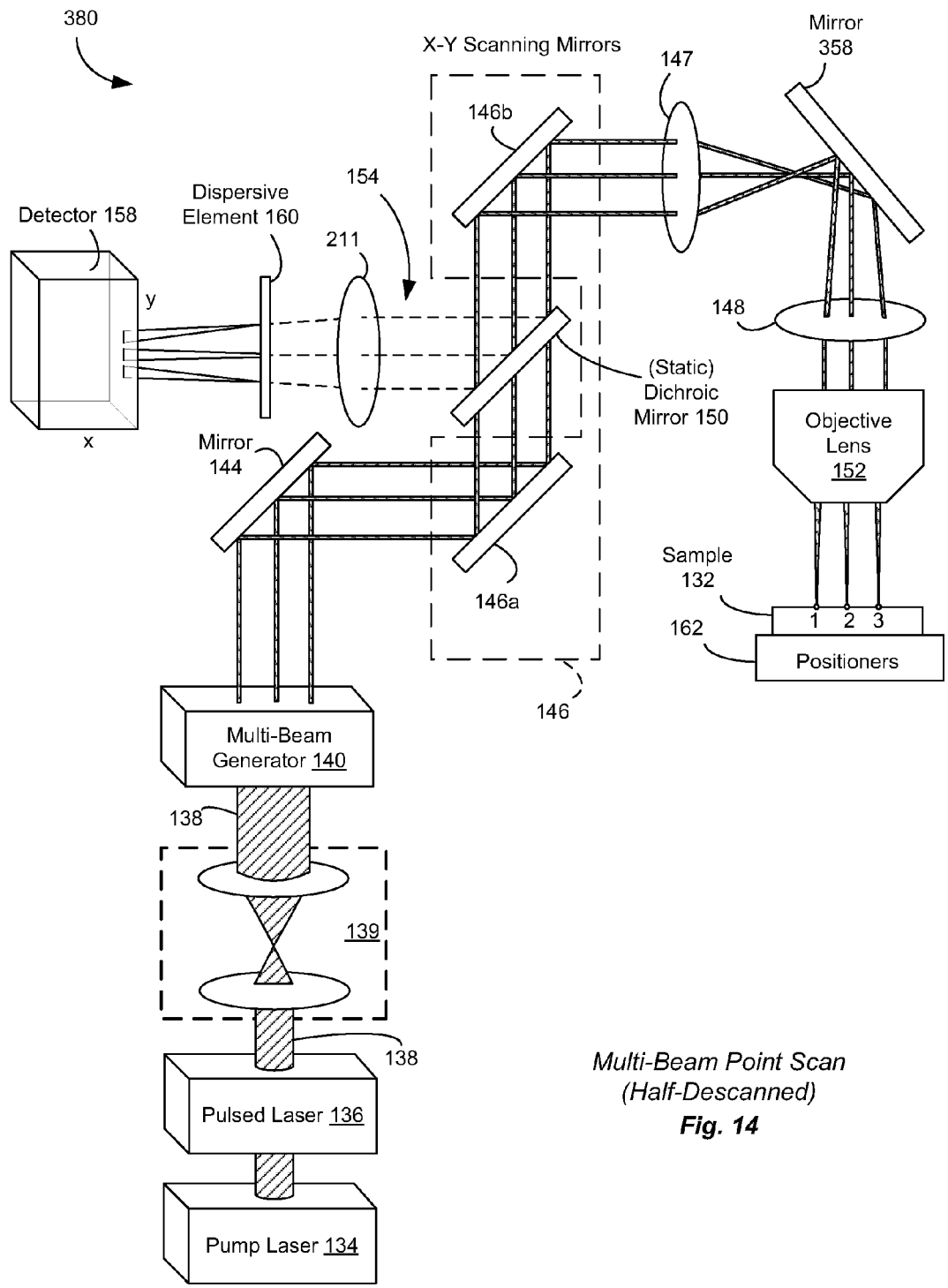
FIG. 14 illustrates a half-descanned, multi-beam point scanning microscope with spectral resolution.

Each of the microscopes 130, 200, and 250 may be implemented as a descanned microscope or half-descanned microscope. For example, FIGS. 12-14 illustrate multi-beam line scanning microscopes, such as microscope 130, implemented as one of a descanned microscope or half-descanned microscope. In FIGS. 12-14, elements similar to those of FIG. 2 are similarly numbered and perform similar functions, unless otherwise noted or necessitated by differences in the respective microscopes.

FIG. 12 illustrates the microscope system 100 implemented as a multi-beam point scanning microscope 350 having a half-descanned arrangement. For simplification, the controller 102, memory 104, user I/O 106, and bus 107 of FIG. 1 are not shown, and. In contrast to the non-descanned microscope 130, the half-descanned microscope 350 includes x-y scanning mirrors 352 having a dichroic (short-pass) scanning mirror 354 and a standard scanning mirror 356. Accordingly, the light beams 142 for scanning the sample 132 are reflected by the dichroic scanning mirror 354 towards the other scanning mirror 356 on route to the sample 132. The fluorescence 154 emitted by the sample 132, however, passes through the dichroic scanning mirror 354 towards the lens 156, dispersive element 160, and detector 158. The microscope 350 further includes a mirror 358 for reflecting the light from the telescope 148 to the objective lens 152.

FIG. 13 illustrates the microscope system 100 implemented as a multi-beam point scanning microscope 370 having a descanned arrangement. For simplification, the controller 102, memory 104, user I/O 106, and bus 107 of FIG. 1 are not shown. In the descanned microscope 370, the dichroic (long pass) mirror 150 is positioned between the multi-beam generator 140 and the x-y scanning mirrors 146. Accordingly, the light beams 142 for scanning the sample 132 are passed through the dichroic mirror 150 towards the scanning mirrors 146 on route to the sample 132. The fluorescence 154 emitted by the sample 132, however, is reflected by the dichroic scanning mirror 150 towards the lens 156, dispersive element 160, and detector 158.

FIG. 14 illustrates the microscope system 100 implemented as a multi-beam point scanning microscope 380 having a half-descanned arrangement. For simplification, the controller 102, memory 104, user I/O 106, and bus 107 of FIG. 1 are not shown. In the half-descanned microscope 380, the dichroic (short pass) mirror 150 is positioned between the scanning mirrors 146a and 146b. The dichroic mirror 150 remains static and is not scanned, in contrast to the dichroic mirror 354 of FIG. 12. Accordingly, the light beams 142 for scanning the sample 132 are passed through the dichroic mirror 150 towards the scanning mirrors 146b on route to the sample 132. The fluorescence 154 emitted by the sample 132, however, is reflected by the dichroic mirror 150 towards the lens 156, dispersive element 160, and detector 158. Since the fluorescence 154 is only scanned across the detector 158 by one of the scanning mirrors (scanning mirror 146b), the fluorescence 154 is scanned across the detector 158 in one of the x- and y-dimensions, but not both the x- and y-dimensions.

As noted above, the single beam line scanning microscope 200 and the multi-beam line scan microscope 250 may be implemented as a descanned microscope or half-descanned microscope. For instance, for a descanned or half-descanned single beam line scanning microscope, the flat mirror 144 of FIGS. 12-14 may be replaced with the curved mirror 202. For a descanned or half-descanned multi-beam line scanning microscope, the flat mirror 144 of FIGS. 12-14 may be replaced with one or more curved mirrors 202 or other beam point to beam line converters. Also, as previously noted, the curved mirrors 202 may be deformable mirrors (see, e.g., FIGS. 10A-B) or non-deformable mirrors.

A standard camera includes a pixel array that is square-shaped, such as a 512×512 pixel array. Generally, pixel data for the entire array is transmitted for each image of the camera. Such a camera may be used as the detector 158 in embodiments of the above-noted microscopes. The detector 158 includes a generally planar detection surface including an array of detector elements (i.e., pixels) that convert energy (e.g., light) into electrical signals for output to an imaging device (e.g., controller 102 and/or memory 104). The electrical signals may then be interpreted, combined, filtered, and/or organized to generate an image. The electrical signals for each pixel may include a digital encoding, such as a series of binary bits, which represent characteristics of the light received by the particular pixel. The electrical signals output by the pixel array may be referred to collectively as "pixel data." The time to transmit pixel data from the pixel array to another device (e.g., the controller 102) is a function of the number of pixels in the array. As the pixel array size increases, the time to transmit the pixel data increases. The time to transmit the pixel data can be a speed limiting factor for scanning using the above-noted microscopes. Accordingly, reducing the pixel data transmission time may improve microscope scanning speed.

Figure 15:
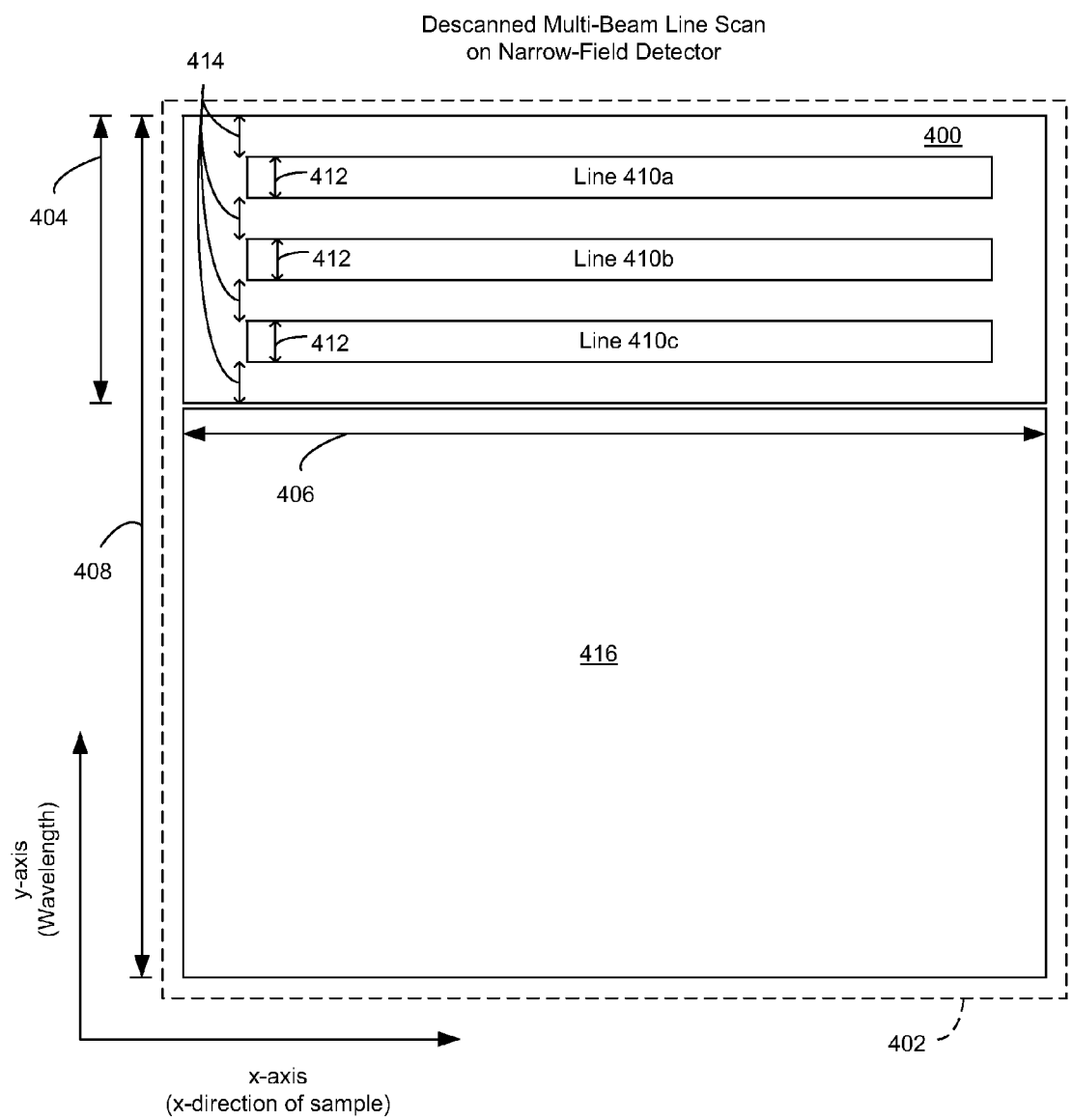
FIG. 15 illustrates a descanned multi-beam line scan on a narrow-field camera.

FIG. 15 illustrates a narrow detector 400 overlaid on a standard, square-shaped pixel array 402. The narrow detector 400 includes a width 404 along the y-dimension and a length 406 along the x-dimension. A standard, square-shaped pixel array 402 includes a width 408 along the y-dimension and the same length 406 along the x-dimension as the narrow detector 400. The width 408 is substantially equal to the length 406. The width 404 of the narrow detector 400, however, is significantly less than the length 406. For instance, the width 404 may be half of the length 406, a third of the length 406, a quarter of the length 406, an eighth of the length 406, a sixteenth of the length, or other sizes. Generally, the lower size limit of the width 404 is constrained by the size of the wavelength spectra in the y-dimension of the beam lines 410a-c plus the additional spacing needed between the camera boundaries and the beam points or lines to prevent light from missing the camera and from overlap. For instance, in the case of the narrow detector 400 illustrated in FIG. 15, the lower limit of the width 404 is the sum of the width of the lines 412 and the spacings 414.

The narrow detector 400, therefore, has significantly fewer pixels than a square-shaped pixel array 402. Accordingly, the time to transmit pixel data from the narrow detector 400 to the controller 102 or memory 104 is significantly less than the time to transmit pixel data from a camera having a square-shaped pixel array.

In some embodiments, the narrow detector 400 is constructed to physically include a narrow array of pixels as described above. However, in some embodiments, the narrow detector 400 is implemented by ignoring the additional pixels in an area 416 of the square-shaped pixel array 402, or by configuring the narrow detector 400 to not output the pixel data from the pixels in the area 416. In the case of ignoring the pixels area 416, the narrow detector 400 and associated microscope may be configured to initiate a new image capture before the output of the undesired pixel data of the pixel area 416 completes, but after the desired pixel data from the narrow detector 400 is received.

The narrow detector 400 may be used as detector 158 in the above-described descanned microscope 370 and half-descanned microscopes 350 and 380 because the beam lines or points received by the detector 158 are static in the y-dimension. For instance, the imprint of a multi-beam line scan on the narrow detector 400 is illustrated in FIG. 15. The lines 410a-c remain static over the course of a scan of the sample 132, and are not scanned along the detector 158. The static position of the lines 410a-c contrasts with the non-descanned implementations, such as shown in FIG. 8B. Additionally, in the beam point scanning embodiments of the half-descanned microscope 380, the beam points are scanned in the x-direction of the narrow detector 400 and remain static in the y-direction. Accordingly, the pixel data from the pixel area 416 may be unnecessary in these implementations.

Figure 16A:
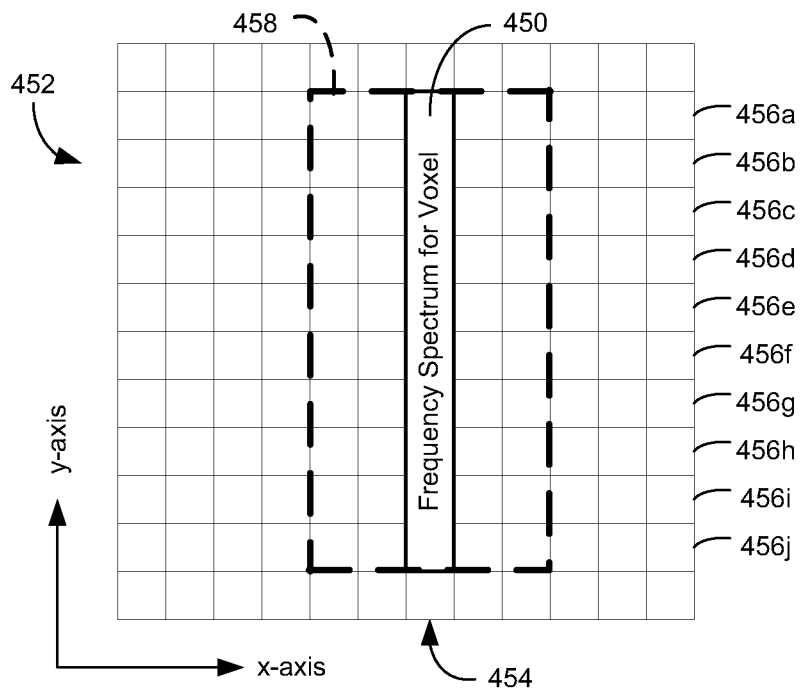
FIGS. 16A-B illustrate a high resolution binning technique.

FIG. 16A illustrates an ideal imprint of a wavelength spectrum 450 received by an array of pixels 452 caused by a beam point emitted from a sample, such as one of the fluorescence beam points 154 on the detector 158. As shown, the wavelength spectrum 450 occupies a single pixel column 454, which corresponds to a particular x-position of a sample (e.g., sample 132). The wavelength spectrum 450 occupies a plurality of rows 456 along the y-axis, each row corresponding to one or more distinct wavelengths. For instance, row 456a may correspond to the shortest wavelength(s), and row 456j may correspond to the longest wavelength(s).

However, an actual imprint 458 of the wavelength spectrum 450 on the pixel array 452 spreads over into neighboring pixel columns; this spread is usually caused by the point spread function of the microscope, which is an intrinsic property of imaging systems. An image generated based only on the light received by column 454 may be less accurate in that the image does not represent all of the light received by the pixel array 452 for a particular x-position of the sample. Additionally, light originating from the same column in the sample, which should ideally be projected onto wavelength spectrum 450, is projected onto adjacent columns within the actual imprint 458, thereby introducing image blur at those columns.

Figure 16B:
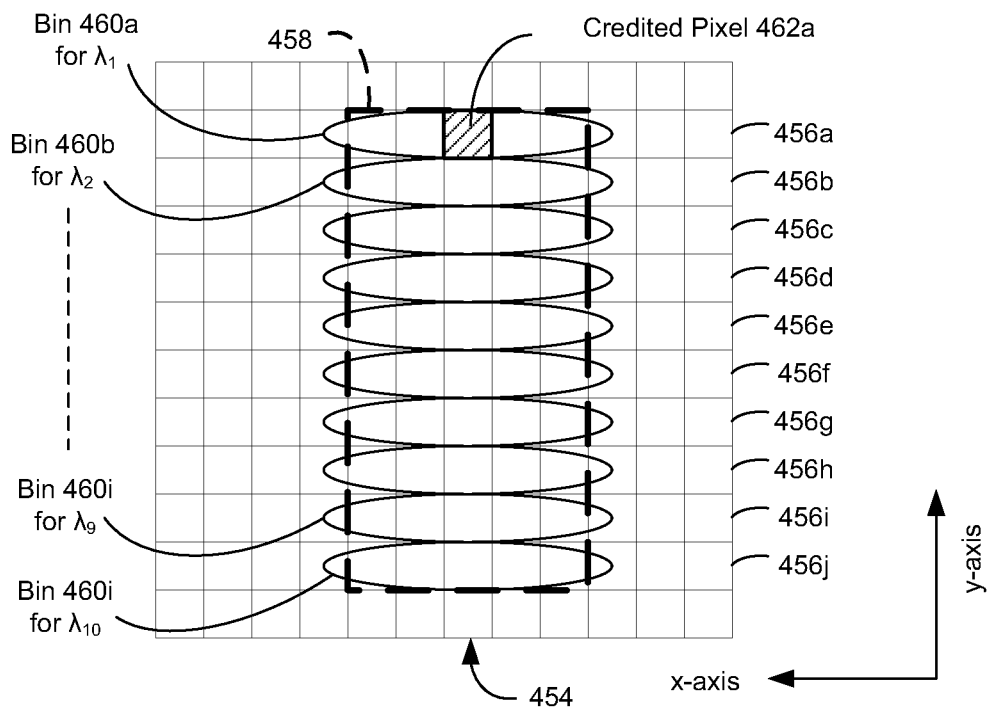

FIG. 16B illustrates a first binning technique to address the spread of the wavelength spectrum 450 along the x-axis and to result in more accurate images. For each wavelength range (i.e., row 456), a bin 460 is used to cover multiple pixel columns. In the FIG. 16B example, each bin 460 includes five pixel columns. The value attributed to each row 456a-j of the wavelength spectrum 450 is the sum of the energy received by the pixels within each respective bin 460a-j. Accordingly, the effective pixel size is greater in the x-dimension than it is in the y-dimension (e.g., five pixels wide by one pixel long). The sum of the light received by one of the bins 460 is attributed to a credited pixel (or pixels) 462, which is less than the total number of pixels making up the bin 460. Stated another way, the size of the bin 462 in the x-dimension (corresponding to the x-direction of the sample) is larger than the size of the credited pixel(s) 462 in the x-dimension. For instance, the bin 460a includes five pixels, and the light received by the bin of five pixels is summed and, for purposes of generating an image, attributed to one credited pixel 462a. In some embodiments, the number of pixels for each bin 460 may be adjusted, e.g., based on the actual spread of the wavelength spectrum 450. For instance, each bin 460 may be three pixels wide, ten pixels wide, etc. Additionally, the number of pixels making up the credited pixel(s) 462 may be more than one pixel.

Although the binning technique of FIG. 16B is illustrated with a single beam point scan, the binning technique may also be implemented with a multiple beam point scan. In the multi-beam point scan implementation, a series of the bins 460 is used for each beam point (i.e., for each wavelength spectrum) that is received by the detector 452.

The binning techniques of FIG. 16B may be implemented in software, hardware, or a combination thereof using various components of the system 100. For instance, the imaging module 118 of the controller 102 may receive data for each pixel of the detector and sum the values according to the bins. Additionally, the imaging module 118 may be used to configure the detector 116 such that the pixels of each bin 460 are tied together. The bin 460 of tied together pixels then output a singular data value representative of the cumulative intensity of light received by the particular bin 460. Such an arrangement reduces the signal spread and increases image contrast as, in the instance of FIG. 16B, a single signal from the whole bin 460a is credited to a single pixel (the credited pixel 462a).

Figure 17A:
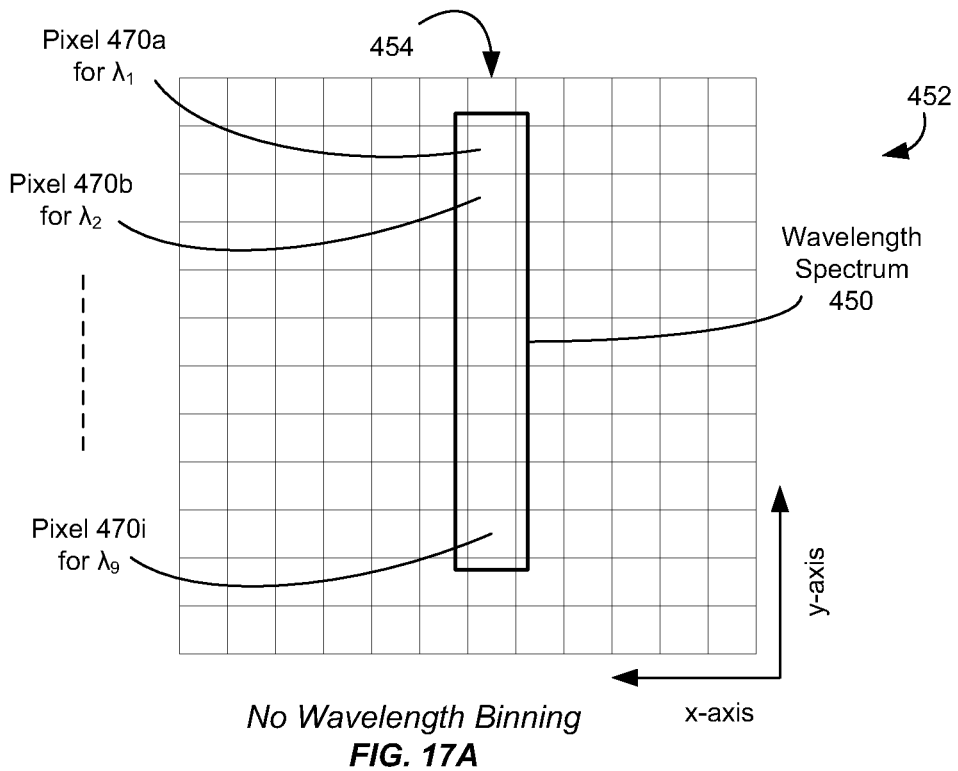
FIGS. 17A-B illustrate a high speed binning technique
Figure 17B:
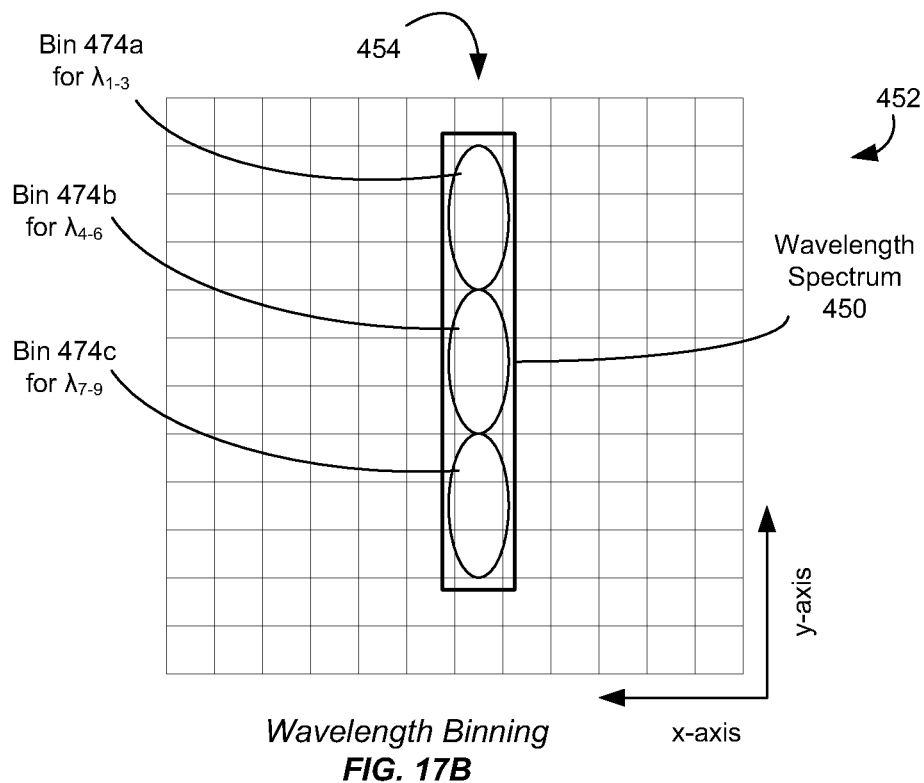

The concept of binning is also applicable in the y-dimension of the detector 452, as illustrated in FIGS. 17A-B. FIGS. 17A-B illustrate the idealized wavelength spectrum 450 on the row 454 of the detector 452. FIG. 17A illustrates a non-binning technique in which each pixel 470 receiving the wavelength spectrum 450 is associated with one or more unique wavelengths. Accordingly, pixel 470a receives wavelength $\lambda_1$, while pixel 470a receives wavelength $\lambda_2$. $\lambda_1$ and $\lambda_2$ may be wavelength ranges, rather than a particular wavelength, where $\lambda_1$ and $\lambda_2$ do not overlap. Each pixel 470 is treated separately and the associated electrical signals of each pixel 470 are output by the detector 452 as a particular data value representing the amount of light emitted from the sample at an associated wavelength (e.g., $\lambda_1$ or $\lambda_2$). Thus, in the example of FIG. 17A, nine data values total are output by pixels 470a-j.

In FIG. 17B, a binning technique in the y-dimension is illustrated. The pixels 470 along the row 454 are combined into bins 474, and each bin 474 is associated with the wavelengths of the pixels 470 making up the bins 474. For example, bin 474a receives wavelengths $\lambda_{1-3}$, because the pixels 470a-c make up the bin 474a, and the pixels 470a-c receive wavelengths $\lambda_{1-3}$, respectively. The electrical signals of each bin 474 are output by the detector 452 as a particular data value representing the amount of light received by the combination of pixels 470 of the particular bin 474. In the example of FIG. 17B, three data value total are output by pixels 470a-j, one for each bin 474a-c. Thus, the amount of data output by the detector 452 is reduced to one third of the data output by the non-binning technique shown in FIG. 17A. Accordingly, the time to transmit pixel data from the detector 452 using the binning technique of FIG. 17B is significantly less than the non-binning technique of FIG. 17A. As noted above, the time to transmit the pixel data can be a speed limiting factor for scanning using the above-noted microscopes. Accordingly, reducing the pixel data transmission time may improve microscope scanning speed. In some embodiments more or fewer than three pixels 470 make up each bin 474, and more or fewer than three bins per x-position on the detector 452 are used.

Although the binning technique of FIG. 17B is illustrated with a single beam point scan, the binning technique may also be implemented with a multiple beam point scan, a beam line scan, and a multiple beam line scan. For instance, in the beam line scan, the wavelength spectrum 450 extends along the x-axis, corresponding with various spatial positions along the x-axis of the sample. Accordingly, for each x-position on the detector, one or more bins 474 of pixels receive light and output data.

Although the detector 452 speed is increased, the wavelength resolution is reduced using the binning technique of FIG. 17B. That is, in FIG. 17A, nine data points over the area of the wavelength spectrum 450 are provided, one per pixel 470. In contrast, only three data points are provided over the same area of the sample using the wavelength binning technique illustrated in FIG. 17B.

The binning techniques of FIG. 17B may be implemented in software, hardware, or a combination thereof using various components of the system 100. For instance, the imaging module 118 may be used to configure the detector 116 such that the pixels of each bin 474 are tied together. The bins 474 of tied together pixels then output a singular data value representative of the cumulative intensity of light received by the particular bin 474. Such an arrangement reduces the data transmission time as described above. Although the system 100 could be arranged such that the imaging module 118 receives data for each pixel of the detector 452, and then sums the values according to the bins, this approach would generally not reduce the number of data transmissions or the time to transmit the data from the detector 452.

The above described microscope systems may be used to implement the methods described below for scanning a sample and identifying particular characteristics of the sample, and for scanning a series of samples and identifying one or more samples within the series of samples that includes the particular characteristics. Detecting samples or portions of samples that emit, scatter, or transmit light at particular wavelengths is useful in identifying samples with or without a particular makeup. For example, a sample may be tagged, through various methods, such as with particular chemical agents. If the sample has a particular makeup, when the sample receives light from the microscope, the tag causes the sample to fluoresce light at particular wavelengths. If the sample does not have the particular makeup, the tag will not cause the sample to fluoresce light at the particular wavelengths. Additionally, in some instances, detecting that a sample does not emit, scatter, or transmit light at a particular wavelength is useful. For instance, a tagged sample that emits fluorescence at a first wavelength, and not a second wavelength, may indicate the makeup of the sample.

The microscopes described herein are operable to provide a complete spectrum from a single scan. A complete spectrum includes, essentially, the entire spectrum of light emitted by the sample, rather than one or a few narrow ranges obtained by using filters. Accordingly, from a single scan, a plurality of wavelengths may be detected as being emitted or not emitted by the sample. For example, results from a single scan of a sample may be analyzed to determine whether fluorescence emitted from the sample has one or more of six various wavelengths.

More particularly, the microscope systems may be used in Förster (or fluorescence) resonance energy transfer ("FRET") analysis. In FRET analysis, the non-radiative transfer of energy from an excited fluorescent molecule (a "donor") to a non-excited acceptor residing nearby is analyzed. For example, a researcher may wish to determine whether a particular ligand binds with a particular receptor of a plasma membrane. The researcher may tag the receptors, such as G protein coupled receptors ("GPCRs"), with fluorescent markers (e.g., yellow tags) and tag ligands with other fluorescent markers (e.g., red tags). If the receptors and ligands bind, the excited donor does not always emit a yellow photon, but sometimes transfers its excitation to a nearby acceptor, which then emits a red photon; hence, the combination of the two colors. Therefore, a user may desire to detect more than a single wavelength (color) emitted by the sample, so as to be able to discriminate between the amount of donor (e.g., yellow) and acceptor (e.g., red) signals. In this way, one may detect possible interactions between the donor-receptor and the acceptor-tagged ligand, or between two different receptors or any other two macromolecules. Additionally, as samples may be highly dynamic, fast acquisition of the image may be desired to reduce the effects of time on the sample over the course of scanning the sample. Using the microscopes system 100, multiple wavelengths of the sample's emitted light may be captured and identified from a single, high-speed scan.

Figure 18B:
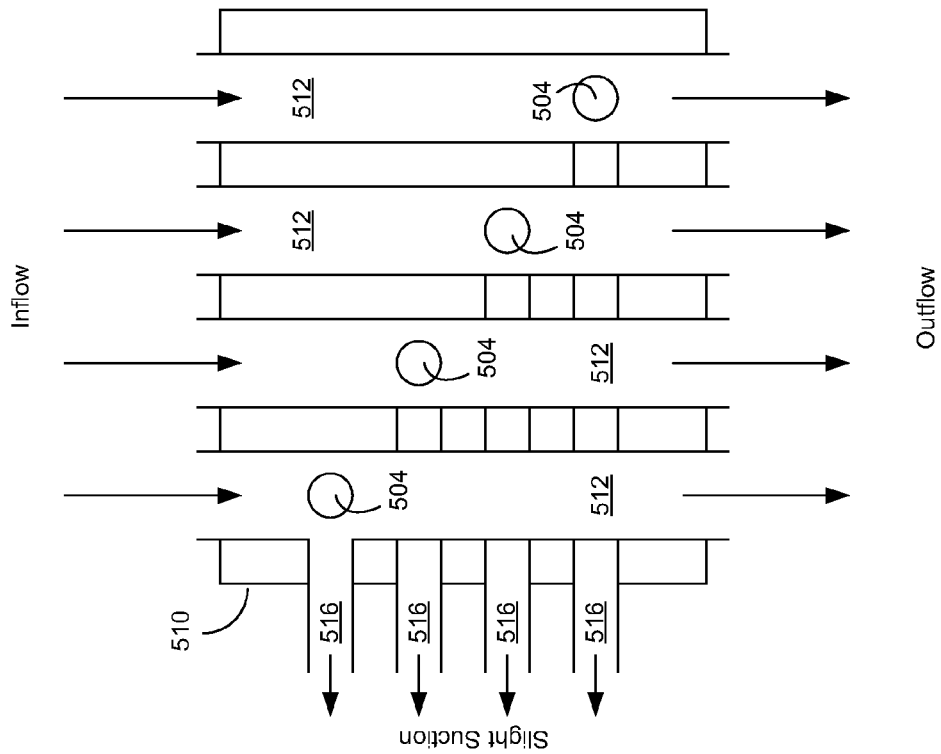
FIGS. 18A-B illustrate techniques for sorting and trapping cells to be scanned.
Figure 18A:
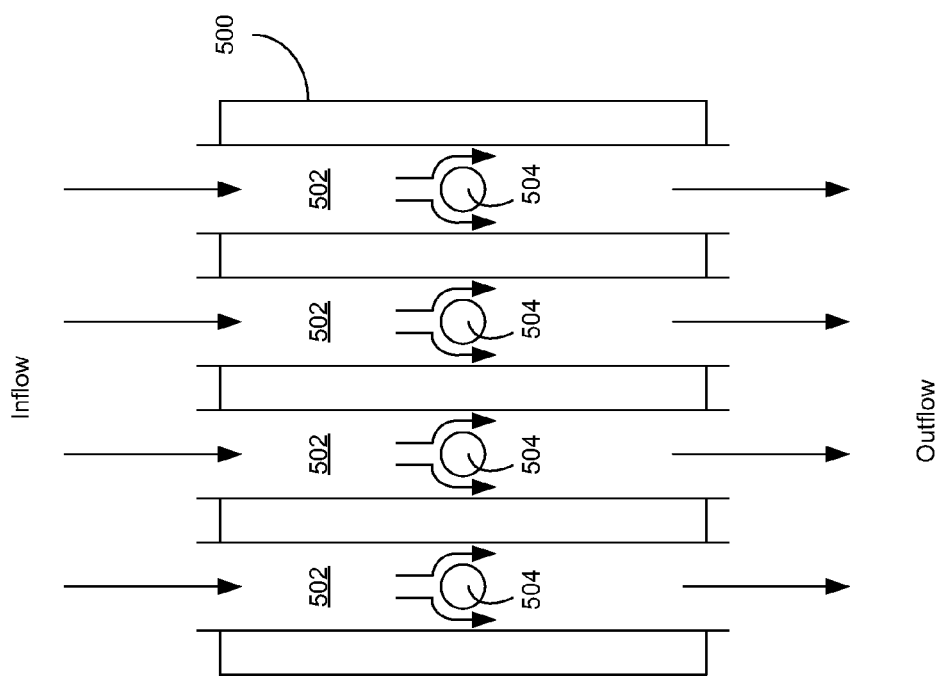

FIGS. 18A-B illustrate techniques for sorting and trapping cells to be scanned using the microscope system 100. FIG. 18A illustrates an optical tweezers technique using a tray 500 including channels 502 for sorting and trapping cells 504. A flow of an outer medium containing the cells is fed through the channels. The cells 504 are then trapped by optical tweezers (not shown) in their respective channels 502 for scanning. The "optical tweezers" use a highly focused laser beam to provide a very small attractive or repulsive force to physically hold the cells 504 in position.

FIG. 18B illustrates a suction technique using a tray 510 including channels 512 for sorting and trapping the cells 504. Each channel 512 includes a suction path 516 to which a slight suction is applied. Accordingly, as the cells 504 flow through the channels 512, the suction through suction path 516 traps the cells 504 in their respective channels 512 for scanning.

Both FIGS. 18A-B result in sorted and trapped cells 504. While the cells 504 are trapped, the microscope system 100 is able to perform a scan of the cells 504. Additionally, while trapped, the composition of the outer medium flowing through the channels 502, 512 may be altered, for instance, by adding ligands or another chemical agent. Accordingly, the cells 504 may be subject to various treatments and analyzed using a micro-analytical assay, such as spectrally resolved fluorescence microscopy and FRET. The trapped cells 504 may be observed for long periods of time while nutrients are continuously supplied through the channels 502. In one example, this observation allows one to determine the location at which proteins are assembled into complexes and to monitor the proteins transport to/from the plasma membrane in the process of membrane recycling. In another example, the trapped cells 504, expressing proteins of interests, may be presented with variable amounts of natural and artificial ligands (including drugs). In this example, the effect of the ligand on receptor oligomerization or on the cell in general can be investigated, in vivo. The number of channels 502, 512 of the trays 500, 510 may be increased or decreased, depending on the field of view of the microscope, the size of the cells, and other factors.

Figure 19:
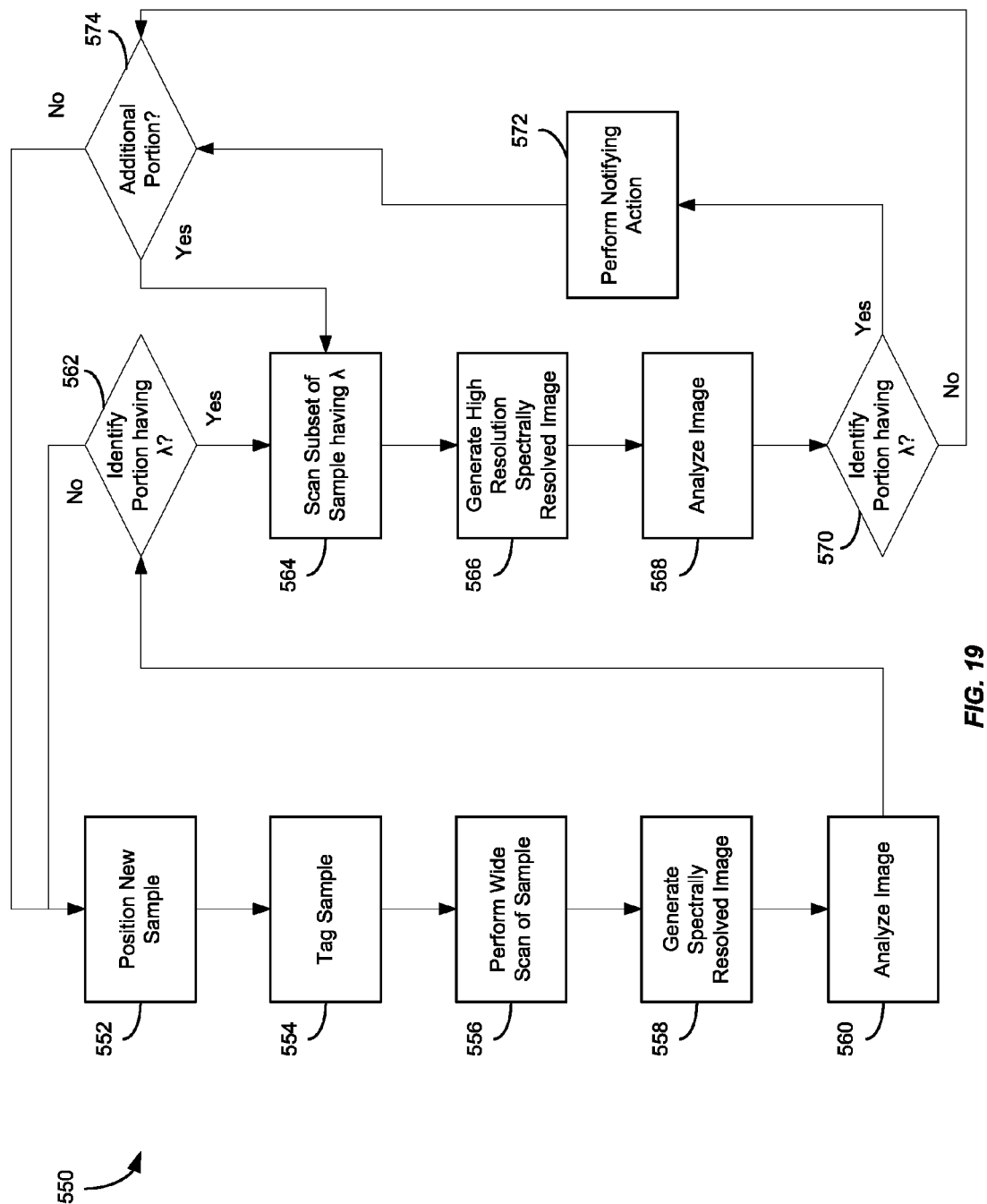
FIG. 19 illustrates a method of scanning and analyzing one or more samples to detect emissions of one or more particular wavelengths.

FIG. 19 depicts a method 550 of analyzing one or more samples to detect emissions of one or more particular wavelengths as a result of a scan using microscope system 100. Unless noted otherwise, reference to microscope 100 is intended to refer to the various microscope embodiments described herein, such as microscopes 130, 200, 250, 350, 370, and 380. Additionally, although the method is described as being implemented with microscopy system 100, the method 550 may also be carried out using other devices.

In step 552, a sample is positioned for scanning by the microscope system 100. For instance, cells 504 may be introduced into channels 502, 512 as depicted in FIGS. 18A-B. In step 554, the sample is subjected to chemical agents. For instance, an outer medium may be introduced into the channels 502, 512 to tag the cells 504. In some embodiments, step 554 may be bypassed if the cell is to be investigated without being subjected to chemical agents or performed before positioning the sample for scanning in step 552.

Figure 20:
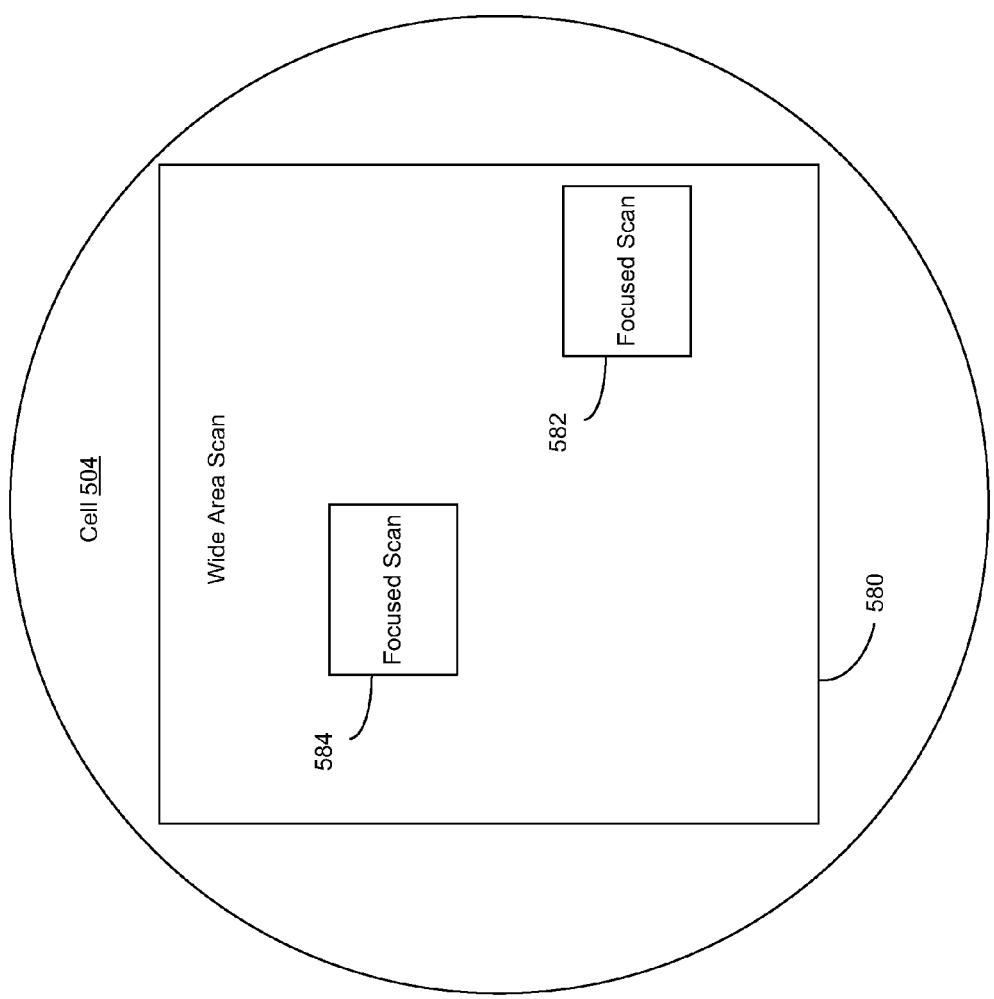
FIG. 20 illustrates scanning areas of a sample undergoing a two-stage scan.

In step 556, with reference to FIGS. 1 and 20, the microscope system 100 is used to perform a fast, wide-area scan of the sample. For a fast, wide-area scan, a low magnification may be used to project an entire slide width onto the detector 116 (e.g., 2500 pixels wide) from a single scan. In FIG. 20, a first portion 580 of one of the cells 504 is scanned using a wide-area scan. Additionally, the fast, wide-area scan may be implemented using the binning technique described with respect to FIG. 17B to further improve the speed. In step 558, the imaging module 118 of the microscope system 100 generates one or more spectrally resolved images based on the pixel data obtained from the detector 116. The pixel data may be used to generate several images of the sample, each depicting a different wavelength range of the fluorescence emitted from the sample. An exemplary image reconstruction technique to generate an image based on pixel data produced by the microscope system 100 is described in U.S. Pat. No. 7,973,927, the description of which is hereby incorporated by reference.

For example, to obtain the fluorescence emission image of the sample for a particular wavelength ($\lambda$n) in the case of a beam line scan, the pixel row from the pixel data corresponding to that particular wavelength $\lambda$n is extracted from each image. Each such row corresponds to a unique y-position of the sample, and the extracted rows are reassembled accordingly to generate an image of the sample at the wavelength $\lambda$n. In the case of a multi-beam implementation where multiple spectra are received by the detector simultaneously, or a binning technique wherein more than one pixel in a particular column corresponds to a particular wavelength band of interest $\lambda$n, multiple pixel rows may be extracted from a single image to form the image of the sample at wavelength $\lambda$n Returning to FIG. 19, in step 560, the analysis module 120 analyzes the image(s) or pixel data to determine whether the sample emitted fluorescence with predetermined characteristics (e.g., at one or more particular wavelengths, at a particular intensity, and over a particularly sized area). In step 562, the controller 102 determines whether the analysis module 120 identified one or more portions of the sample that emitted fluorescence with predetermined characteristics. If no portion is identified, as determined in step 562, the method 550 returns to step 552 to begin analysis of a new sample. If a portion of the sample is identified, as determined in step 562, the method 550 proceeds to step 564.

In step 564, a second portion 582 of the sample is scanned. The second portion 582 is a subset of the first portion scanned in step 556, and corresponds to the portion identified in step 582. The microscope system 100 then performs a high resolution, focused scan of the second portion 582. For instance, the second portion 582 is scanned without using a binning technique, or with using the binning technique of FIG. 16B. The focused scan may be a slower scan than the fast, wide area scan of step 556. In step 566, the imaging module 118 of the microscope system 100 generates one or more spectrally resolved images based on the pixel data obtained from the detector 116.

In step 568, the analysis module 120 analyzes the image(s) or pixel data to determine whether the second portion 582 emitted fluorescence with predetermined characteristics. In step 570, the controller 102 determines whether the analysis module 120 identified the second portion 582 of the sample as having emitted fluorescence with predetermined characteristics. In step 572, if the second portion 582 emitted fluorescence with predetermined characteristics, the controller 102 may perform a notifying action, such as outputting the resulting image(s) to the user I/O 106, storing the image(s) with a flag set, generating an alert or alarm, transmitting the image(s) to remote devices (e.g., personal computers, smart phones, etc.), or take another action to notify or highlight the sample or image(s). An alert may include one or more of a local audible or visual message via the user I/O 106, or an audible or visual message transmitted to a remote device (e.g., via email, text message, automated voice message, etc.).

In step 574, the controller 102 determines whether an additional portion was identified in step 562. If so, the controller 102 proceeds back to step 564 to perform a focused scan and analysis of that portion (e.g., third portion 584). If no additional portions were identified in step 562, the method 550 returns to step 552 to begin analysis of a new sample. The method 550 may repeat until no further samples are available for scanning.

In some embodiments, the generation steps 558 and 566 may include exporting pixel data to a memory 104 or controller 102 for analysis by the analysis module 120 without actually generating an image viewable by a person. Rather, the pixel data is merely received, stored, and/or arranged such that the analysis module 120 may sift through the pixel data to determine whether the pixel data indicates that a portion of the sample emitted fluorescence with predetermined characteristics.

The higher resolution, focused scan of step 564 assists in removing false positives generated by the fast, wide-area scan of step 556. Accordingly, those samples identified in step 562 may be referred to as tentatively positive samples, and those samples identified in step 570 may be referred to as positive samples. For example, the predetermined characteristics of a tentatively positive sample, as identified in step 562, may include two or more markers. Additionally, the focused scan of step 564 results in higher resolution images that may be used to provide more detail (including morphological) of the pertinent portion of the tentatively positive sample to confirm the makeup of the portion (e.g., the identity of a particular cell). The higher resolution images may also be used for later human review and analysis.

A user may store the predetermined characteristics of the fluorescence to be detected in the memory 104 using the user I/O 106, and then may initiate the method 550. Once initiated, the method 550 may be an automated process such that a plurality of samples may be scanned and analyzed, and those samples having particular characteristics may be identified without further user interaction.

Although the microscope system 100 has generally been described as generating images with a spatial (x) dimension and a wavelength (y) dimension of the sample, as noted above, multiple images obtained may be re-constructed via the imaging module 118 to form a series of images, one for each desired frequency range, with a spatial (x) dimension and spatial (y) dimension. See, for example, the image reconstruction techniques described in U.S. Pat. No. 7,973,927. The microscope system 100 may also scan the sample 132 at various depths to produce an additional spatial (z) dimension to the images. Accordingly, 3-D images (x-y-z dimensions) may be generated for each desired frequency range by stacking multiple 2-D (x-y dimension) images generated by the above-noted image reconstruction. In some applications, this 3-D scanning capability allows a specific volume of samples to be scanned much faster than distributing that volume amongst multiple slides for scanning each at a single height in 2-D. Furthermore, samples may be scanned over time to produce a fourth (time) dimension. For example, 2-D and 3-D images generated at time (t)=0, 1, . . . , n, may be streamed in series to show the sample changing over the time period 0 to n.

The microscope system 100 and method 550 enable the rapid identification of rare cells. The microscope system 100 is operable to rapidly scan smears of blood or enriched cells on microscope slides to find and identify rare, differentially stained cells in an overwhelming background of non-target cells. An exemplary rare cell is a fetal cell in maternal blood ("FCMB"), which enables the detection of genetic aberrations during the first trimester of pregnancy without risk to the fetus or mother. In most pregnancies, a few fetal cells pass the placenta to enter the maternal blood stream, reaching concentrations of 0.1 to 100 cells per milliliter of blood. The microscope system 100 enables the rapid identification of these rare fetal cells against a more than million-fold excess of maternal white cells.

Several fetal cell-specific surface markers exist that allow for their differential staining and identification against the background of maternal white blood cells. These markers may be used to enrich fetal cells using magnetic separation. The enriched cell population is then transferred to one or more slides. After labeling with fluorescently tagged fetal-cell-specific surface markers, the location of these cells on the slide are then identified by imaging using the microscope system 100. These slides may then be deproteinized and subjected to fluorescent in situ hybridization (FISH), a process that identifies specific genetic abnormalities in a cellular genome. The microscope system 100 then scans and analyzes the portions of the (now) FISHed slides previously identified to be occupied by a fetal cell. The microscope system 100 then determines the absence, presence and/or multiplicity of specific fluorescent signals. The slides may be automatically loaded for analysis by the microscope system 100 using an automatic slide changer, thereby allowing continuous, fast automated scans of a plurality of samples. Additionally, the analysis of the slides may include execution of the method 550 of FIG. 19.

A similar approach as the one described above for FCMB detection can be applied to the identification of circulating tumor cells for early diagnosis of disease, or for monitoring of recurrence after therapy. Solid tumors initially arising as an organ-confined lesion eventually spread to distant sites through the bloodstream, generating metastases that are mainly responsible for their lethality. Detecting cancer cells that have been shed into peripheral blood provides a powerful and noninvasive approach for diagnosing early disease and assessing the prognosis and therapeutic response. Detecting disseminated rare tumor cells in bone marrow aspirates is equally important for early diagnosis. The medical benefits of early cancer detection are significant; however, the frequency of tumor cells in these tissues is often less than 1 per $10^6$ normal cells, presenting a significant problem for the diagnosing pathologist. The high sensitivity, rapid, and full-color spectral analysis provided by the microscope system 100 enables detection of fluorescently stained rare cells, such as cancer cells, to provide early detection of cancer cells.

The microscope system 100 may also be used to identify stem cells. The CD34+ cell fraction of bone marrow and blood contains the hematopoietic stem cells, which are used in marrow reconstitution following myeloablative therapy. As the stem cells are present in small numbers, accurate quantification presents challenges. For instance, the stem cells occur at a ratio of 1 per million requires counting of 100 million cells in order to detect the 100 target cells with a CV of 10%. The microscope system 100 detects specifically labeled target cells reliably at a ratio far below this, and, accordingly, may be used to detect the hematopoietic stem cells.

Similar to the above-described rare cell detections, the microscope system 100 may also be used in the identification of genetic aberrations by multi-color FISH in interphase cells for prenatal or cancer cytogenetics, the rapid analysis of tissue sections after immuno-staining, cancer cells circulating in blood or intermixed with tissue, microbes circulating in blood, and viruses circulating in blood. Exemplary microbes include bacteria, fungi, tuberculosis (TB), malaria, and similar organisms. Exemplary viruses include human immunodeficiency virus (HIV) and hepatitis.

The microscope system 100 may also be used in the study of microarrays and tissue arrays, which can require a relatively large scan area in order to allow for the analysis of thousands of individual location ("spots"). In the case of DNA arrays, each spot represents the location of an immobilized capture probe, and, in the case of protein arrays, each spot represents either a specific antibody or a specific target protein. For these types of arrays, the spot size is typically about 100 micron diameter, and the analysis typically involves a determination of the average pixel intensity per spot in one or two colors.

Tissue microarrays, in contrast, are produced using a hollow needle to remove tissue cores as small as 0.6 mm in diameter from regions of interest in paraffin-embedded tissues, such as clinical biopsies or tumor samples. These tissue cores are then inserted in a recipient paraffin block in a precisely spaced, array pattern. Sections from this block are cut using a microtome, mounted on a microscope slide, and then analyzed using histological analysis. Each microarray block can be cut into 100-500 sections, which can be subjected to independent tests. The microscope system 100 may be employed to test the tissue microarrays using immunohistochemistry and fluorescent in situ hybridization (FISH).

Analysis of tissue microarrays by the microscope system 100 is particularly useful in analysis of cancer samples. Tissue arrays contain protein, RNA, and DNA molecules, thus providing high throughput platforms for the rapid analysis of molecular markers associated with disease diagnosis, prognosis, and therapeutics in patients. The analysis can be used to validate clinical relevance of potential biological targets in the development of diagnostics and therapeutics and to study new protein markers and genes. The analysis of tissue sections generally requires a much higher resolution than DNA and protein arrays, and also includes analysis of sub-cellular features within each section. In some embodiments, the microscope system 100 enables diffraction limited resolution (i.e., one micron or less), and spectral resolution selectable between 2 and 20 nm, with an acquisition speed of about two minutes per one full set of spectral images with a 15 mm×15 mm scan area, or fourteen minutes per 22 mm×71.5 mm area, with a complete wavelength spectrum.

The scanning throughput rate of the microscope system 100 may be further adjusted by altering the objective power (e.g., magnification of the objective lens 152) and the stage step-size. For example, using a 40× objective, the scan area covers a 0.5 millimeter by 0.192 mm area and may visualize about 100 cells. Using a 20× objective the scan area is twice that of the 40× objective, making about 200 cells visible. Finally, using a 10× objective, up to 600 cells may be visible. Therefore, to increase the throughput rate, a lower power objective, such as 10×, would serve to decrease scan time for each specimen, because more area is covered by a scan.

Additionally, a reduction in resolution, or reduction in over-sampling, is another way of decreasing scan time. If the stage step size is increased, the spatial resolution is reduced, but more cells are visualized, increasing sample size. For example, if the step size is increased to 8 microns, the step size allows scanning of an entire microtiter well in a single scan field.

Figure 21:
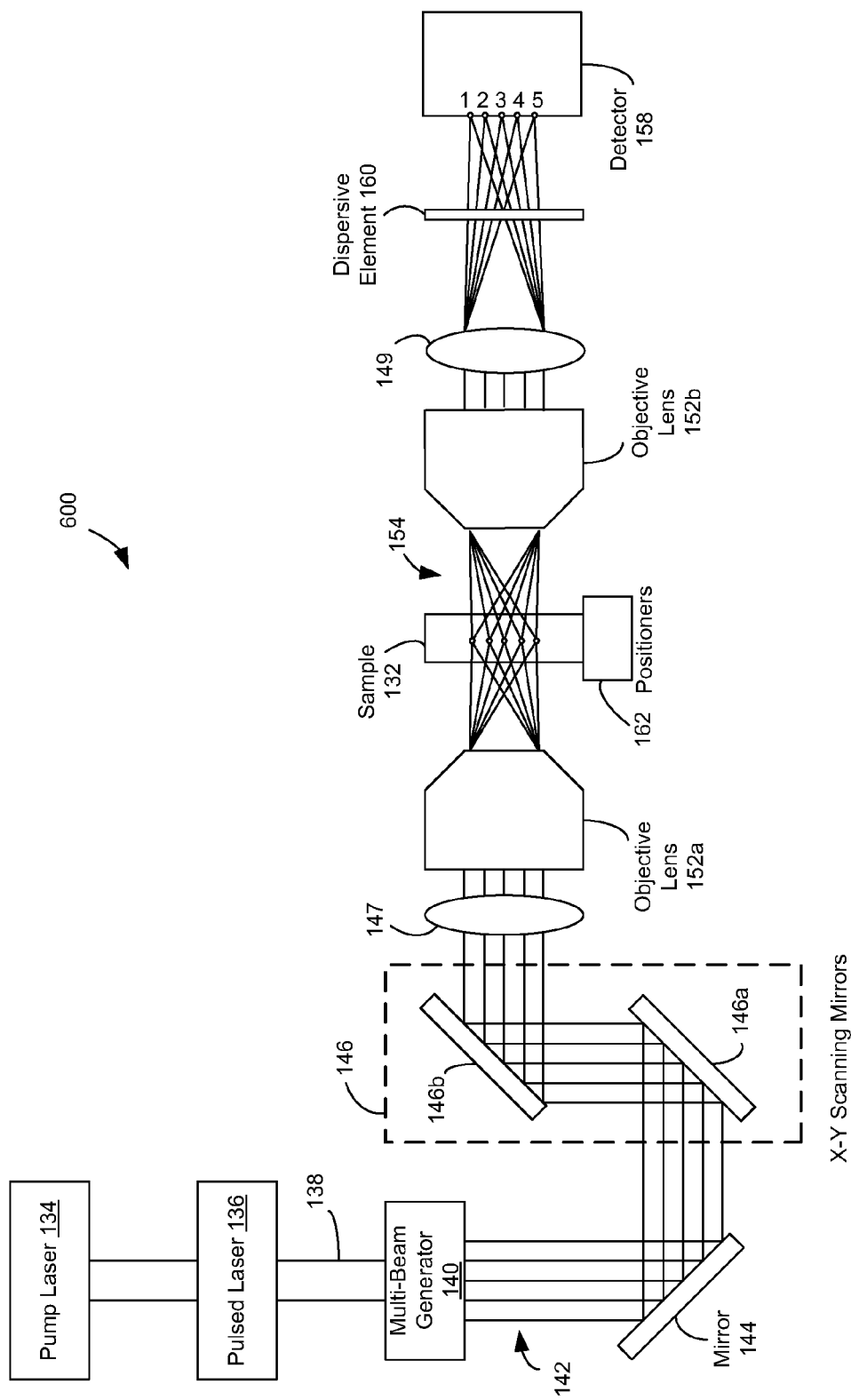
FIG. 21 illustrates a high speed microscope with transmission imaging.

FIG. 21 illustrates the microscope system 100 implemented as a transmission microscope 600 for transmission imaging. As shown in FIG. 21, the transmission microscope 600 includes components previously described with respect to the above-noted microscopes (e.g., microscopes 130, 200, 250, 350, 370, and 380). In contrast to the above-noted microscopes, when the transmission microscope 600 scans light across the sample 132, the fluorescence 154 emitted from the sample 132 is received by a second objective lens 152b that is on the opposite side of the sample 132 from which the beams 142 are received. Accordingly, the fluorescence 154 emitted does not go back towards the objective lens 152a from which the beams 142 came.

The other above-noted, non-descanning microscopes 200 and 250 may also be implemented as transmission imaging microscopes by adding a second objective lens 152b as described with respect to transmission microscope 600.

Figure 22:
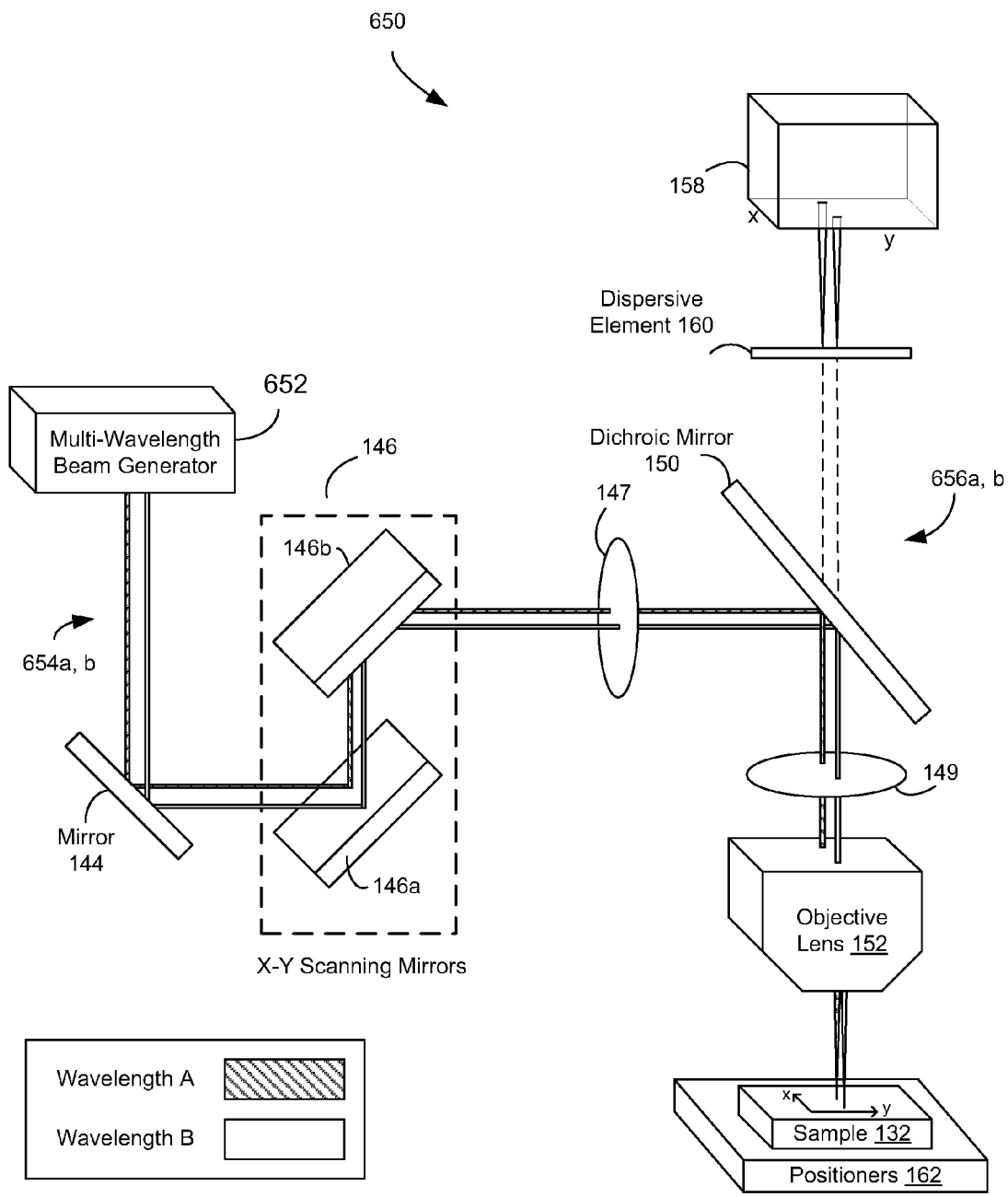
FIG. 22 illustrates a high speed microscope with excitation beams having various wavelengths.
Figure 24A:
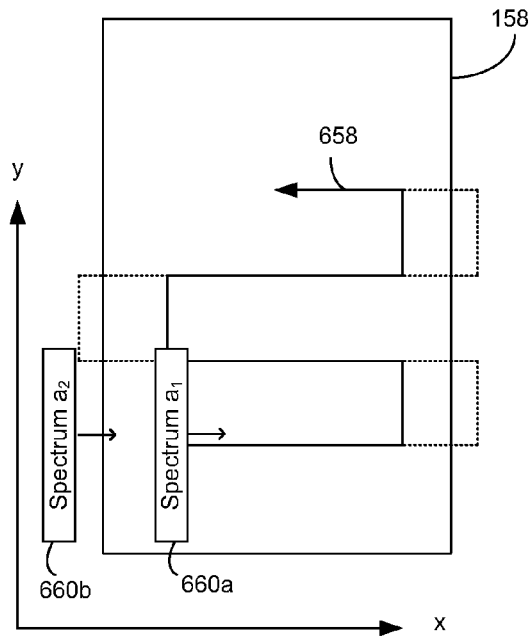
FIG. 24A-D illustrates a detector receive emitted energy from a sample excited using beams with various wavelengths.
Figure 24B:
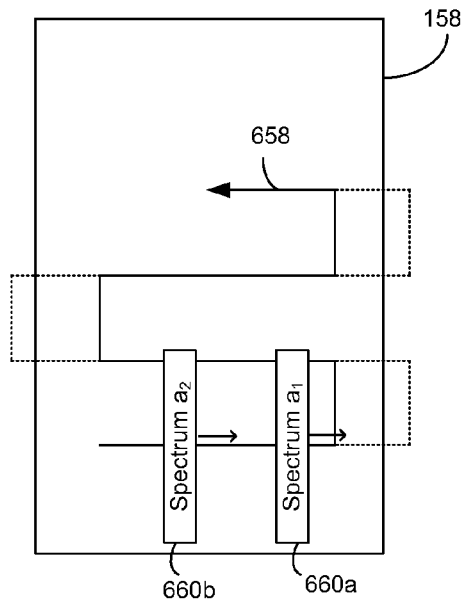
Figure 24C:
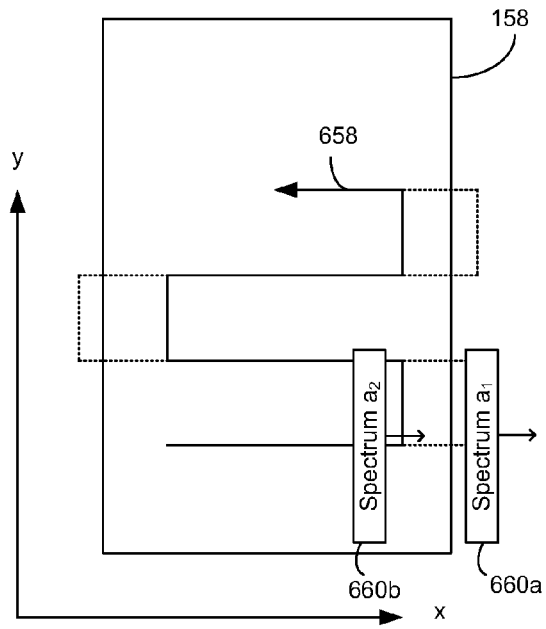
Figure 24D:
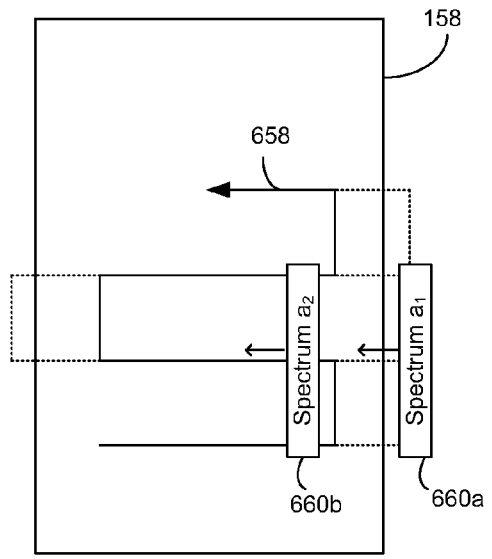

FIG. 22 illustrates the microscope system 100 implemented as a multi-excitation beam scanning microscope 650 for analyzing sample 132. For simplification, the controller 102, memory 104, user I/O 106, and bus 107 of FIG. 1 are not shown. As shown in FIG. 21, the microscope 650 includes components previously described with respect to the above-noted microscopes (e.g., microscopes 130, 200, 250, 350, 370, and 380, and 600).

The microscope 650 includes a multi-wavelength beam generator 652, which outputs a first wavelength light beam 654a and a second wavelength light beam 654b. The first and second wavelength light beams 654a-b having a first and second wavelength, respectively. The light beams 654a-b are reflected by mirror 144, scanned by the scanning mirrors 146, and focused by the lens 147. The dichroic mirror 150 reflects the light beams 654a-b toward the lens 149, which collimates the light beams 654a-b. The objective lens 152 focuses the light beams 654a-b to beam points on the sample 132. The beam points are spaced apart in the x-direction, but are at the same position in the y-dimension, as will be described in further detail with respect to FIGS. 23A-D. In response to the light beams 654a-b, the sample 132 emits fluorescence beams 656a-b towards the objective lens 152 and lens 149. The lens 149 focuses each emitted fluorescence beams 656a-b to a point on the detector 158. The fluorescence beams 656a-b, however, first pass through the short-pass dichroic mirror 150 and a light dispersive element 160. The short-pass dichroic mirror 150 allows visible light to pass through, while reflecting most of the infrared light components of the emitted fluorescence beams 656a-b. The dispersive element 160 disperses the light into its spectral components to form a continuous spectrum of varying wavelengths that spread in the y-direction of the detector 158. The dispersed light beams 654a-b impinge the detector as spectra at the same y-position, but spaced apart in the x-direction (see, e.g., FIGS. 24A-D).

The multi-wavelength beam generator 652 may be implemented using various techniques. For instance, the multi-wavelength beam generator 652 may include two light sources that each emits a particular wavelength beam. Additionally, the multi-wavelength beam generator 652 may include a single laser that has two output beams, each with a different wavelength. Alternatively, multi-wavelength beam generator 652 may include a broadband light source in conjunction with one or more of filters, gratings, prisms, dichroic mirrors, etc. to produce two light beams, each having a different wavelength. Using different wavelengths to excite the sample enables the microscope 650 to provide spectral resolution in the excitation channel.

FIGS. 23A-D illustrate a multi-excitation beam scan on the sample 132. The objective lens 152 focuses the light beams 654a and 654b on the sample as points ($a_1$ and $a_2$, respectively). As illustrated in FIGS. 23A-D, the light beams 654a and 654b are at the same y position on the sample 132, but are spaced apart in the x-direction. The light beams 654a and 654b both follow the same path 658 to scan the sample and remain in lock-step (i.e., at the same distance apart along the x-dimension and at the same y-position). FIG. 23A illustrates an initial position, while FIGS. 23B through 23D illustrate the light beams 654a-b in various positions along the path 658. To enable the light beam 654a to reach the left-most portions of the sample, the light beam 654b is temporarily focused on a point to the left of the scan area each time the light beams 654a and 654b reach the left side of the sample 132 (see, e.g., FIG. 23A). To enable the light beam 654b to reach the rightmost portions of the sample, the light beam 654b is temporarily focused on a point to the right of the scan area each time the light beams 654a and 654b reach the right side of the sample 132 (see, e.g., FIGS. 23C and 23D). Accordingly, as the light beams 654a-b scan across the sample 132 to the right, the light beam 654b trails the light beam 654a, but as the light beams 654a-b scan across the sample 132 to the left, the light beam 654a trails the light beam 654b. Thus, the light beam 654a and 654b alternate between leading and trailing positions along the path 658.

FIGS. 24A-D illustrate a multi-excitation beam scan on the detector 158. As noted above, the emitted fluorescence beams 656a and 656b pass through a dispersive element 160 that disperse the beams into their spectral components, which form spectra 660a and b. The spectra 660a and 660b have a line shape extending along the y-direction, and each is positioned at the same y-position and spaced apart in the x-direction. Each spectrum 660 is formed of a continuous spread of the emitted fluorescence over a range of wavelengths. Each point along the y-axis of the spectrum 660 includes components of the emitted fluorescence at a different wavelength. For instance, the upper/top portion of the spectrum 660 may include the larger wavelengths components, while the lower/bottom portion includes the shorter wavelength components. Similar to the beams 654a and 654b, the spectra 660a and 660b generally follow the same the path 658. Pixel data is obtained from the detector 158 as the spectra 660a and 660b reach each point along the scan path 658, which corresponds to the beam points 654a-b reaching each position of the sample 132 along scan path 658.

In some embodiments, one or more additional excitation beams are included, each having a particular wavelength and spaced apart in the x-direction from the light beams 654a and 654b, but at the same y-position, on the sample 132. In some embodiments, the excitation light beams 654a-b are replicated at different y-positions on the sample 132 to combine the concepts of the microscope 650 with the multi-beam point scan of the microscope 130 (FIG. 2). Accordingly, as shown in FIGS. 25A-B, additional excitation light beams 662a and 662b are provided on the sample 132. The light beam 662a has the same wavelength as light beam 654a, and the light beam 662b has the same wavelength as the light beam 654b. The light beams 662a and b follow a path 664, which is similar to, but displaced in the y-direction from, the path 658. The light beams 662a-b cause the sample to emit fluorescent beams, which are dispersed by the dispersive element 160 and impinge the detector 158 as spectra 666a-b. The spectra 666a-b follow the path 664 on the detector 158, similar to the spectra 660a-b following the path 658. By introducing the additional light beams 662a-b, the scan time of the sample 132 may be reduced relative to the embodiments of FIG. 22. Although shown in a nondescanned implementation, the microscope 650 may also be a arranged in a descanned or half-descanned implementation.

In some embodiments, the various microscopes (e.g., 130, 200, 250, 350, 370, 380, 600 and 650) include additional telescopes, lenses, filters, etc. to focus and transmit light between the various components illustrated, such as between the tube lens 156 and the detector 158. Additionally, although the sample 132 is often described above as emitting fluorescence (e.g., fluorescence 154, 210, and 256), the energy emitted by the sample 132 in response to a scan for detection by the detector 158 may include one or more of fluorescence, elastically scattered light (i.e., Raman), second harmonic signals, and third harmonic signals, or other light types.

Thus, the invention provides, among other things, a system and method of high-speed microscopy using a microscope with spectral resolution. The microscope may include one of a multi-beam point scanning microscope, a single beam line scanning microscope, and a multi-beam line scanning microscope. The systems and methods provide improved scanning speeds, rendering the microscopes advantageous in a variety of applications, including medical research and diagnostics. Various features and advantages of the invention are set forth in the following claims.

What is claimed is:

1. A microscope for generating a multi-dimensional, spectrally resolved image, the microscope comprising:
   a light source that generates a pulsed light beam;
   a curved mirror that reflects the pulsed light beam as a light beam line;
   a scanning mechanism that scans the light beam line across a sample to cause the sample to emit energy;
   a dispersive element that receives the emitted energy from the sample and disperses the emitted energy into spectral components that form continuous spectrum area, the continuous spectrum area corresponding to the light beam line; and
   a detector that receives the continuous spectrum.

2. The microscope of claim 1, further comprising a second curved mirror that reflects the pulsed light beam as a second light beam line, wherein
   the scanning mechanism scans the second light beam line across the sample to cause the sample to emit additional energy,
   the dispersive element receives the additional emitted energy from the sample and disperses the additional energy into second spectral components that form a second continuous spectrum area, the second continuous spectrum area corresponding to the second light beam line, and
   the detector receives the second continuous spectrum.

3. The microscope of claim 1, wherein the scanning mechanism includes computer-controlled x-y scanning mirrors positioned between the light source and the sample.

4. The microscope of claim 1, wherein the scanning mechanism includes computer-controlled sample positioners that move the sample to cause the light beam line to scan the sample.

5. The microscope of claim 1, wherein the microscope is a two-photon microscope.

6. The microscope of claim 1, wherein the curved mirror is a deformable mirror shaped by control signals from a mirror controller.

7. The microscope of claim 6, wherein the shape of the deformable mirror is adjusted based on feedback from a light sensor related to aberrations in the pulsed light beam.

8. The microscope of claim 1, further comprising an imaging module for receiving pixel data output by the detector and generating one or more images based on the pixel data.

9. The microscope of claim 1, wherein the emitted energy is one of fluorescence, elastically scattered light, second harmonic signals, and third harmonic signals.

10. The microscope of claim 1, further comprising
    a first objective positioned between the scanning mechanism and the sample, wherein the first objective receives the light beam line from the scanning mechanism and transmits the light beam line to the sample, and
    a second objective positioned between the sample and the dispersive element, wherein the second objective receives the emitted energy from the sample and transmits the emitted energy to the dispersive element.

11. A microscope for generating a multi-dimensional, spectrally resolved image, the microscope comprising:
- a light source that generates a pulsed light beam;
- a multi-beam generator that receives the pulsed light beam and emits multiple light beams;
- a light beam line generator that receives the multiple light beams and emits multiple light beam lines;
- a scanning mechanism that simultaneously scans the multiple light beam lines across a sample to cause the sample to emit energy;
- a dispersive element that receives the emitted energy from the sample and disperses the emitted energy into spectral components that form continuous spectrum areas, each continuous spectrum area corresponding to one of the multiple light beam lines; and
- a detector that receives each continuous spectrum simultaneously.

12. The microscope of claim 11, wherein the multi-beam generator is a grating.

13. The microscope of claim 11, wherein the multi-beam generator is one of a beam splitter and an array of lenses.

14. The microscope of claim 11, wherein the light beam line generator includes a first curved mirror and a second curved mirror.

15. The microscope of claim 11, wherein the light beam line generator includes a first lens and a second lens.

16. The microscope of claim 11, wherein the emitted energy is one of fluorescence, elastically scattered light, second harmonic signals, and third harmonic signals.

17. The microscope of claim 11, further comprising
- a first objective positioned between the scanning mechanism and the sample, wherein the first objective receives the light beam lines from the scanning mechanism and transmits the light beam lines to the sample, and
- a second objective positioned between the sample and the dispersive element, wherein the second objective receives the emitted energy from the sample and transmits the emitted energy to the dispersive element.

18. A microscope for generating a multi-dimensional, spectrally resolved image, the microscope comprising:
- a light source that generates a pulsed light beam;
- a multi-beam generator that receives the pulsed light beam and emits multiple light beams;
- a scanning mechanism that simultaneously scans the multiple light beams across a sample, the sample emitting energy corresponding to each of the multiple light beams;
- a dispersive element that receives the emitted energy from the sample and disperses the emitted energy into spectral components that form continuous spectrum lines, each continuous spectrum line corresponding to one of the multiple light beams; and
- a detector that receives each continuous spectrum line simultaneously.

19. The microscope of claim 18, wherein the multi-beam generator is a grating.

20. The microscope of claim 18, wherein the scanning mechanism includes one of
- computer-controlled x-y scanning mirrors positioned between the light source and the sample, and
- computer-controlled sample positioners that move the sample to cause the multiple light beams to scan the sample.

21. The microscope of claim 18, wherein the microscope is a two-photon microscope.

22. The microscope of claim 18, wherein the emitted energy is one of fluorescence, elastically scattered light, second harmonic signals, and third harmonic signals.

23. The microscope of claim 18, further comprising
- a first objective positioned between the scanning mechanism and the sample, wherein the first objective receives the light beams from the scanning mechanism and transmits the light beams as light beam points to the sample, and
- a second objective positioned between the sample and the dispersive element, wherein the second objective receives the emitted energy from the sample and transmits the emitted energy to the dispersive element.

24. The microscope of claim 18, wherein the multiple light beams include at least a first light beam with a first wavelength, and a second light beam having a second wavelength.

25. The microscope of claim 24, wherein the first light beam follows a path when scanned across the sample and the second light beam follows the path when scanned across the sample.

26. The microscope of claim 24, wherein the first light beam and the second light beam alternate between leading and trailing positions along the path.

27. The microscope of claim 24, wherein the first light beam is scanned across the sample in an x-direction at a y-position, and the second light beam is simultaneously scanned across the sample in the x-direction at the y-position, the second light beam being offset in the x-direction from the first light beam.

28. The microscope of claim 24, wherein the continuous spectrum line for the first light beam follows a path across the detector during the scan, and the continuous spectrum line for the second light beam follows the path across the detector during the scan.

29. The microscope of claim 24, wherein the continuous spectrum line for the first light beam and the continuous spectrum line for the second light beam alternate between leading and trailing positions along the path.

30. A method of generating a multi-dimensional, spectrally resolved image, the method comprising:
- generating a pulsed light beam;
- reflecting, by a curved mirror, the pulsed light beam as a light beam line;
- scanning the light beam across a sample to cause the sample to emit energy;
- dispersing the emitted energy from the sample into spectral components that form a continuous spectrum area, the continuous spectrum area corresponding to each point along the light beam line; and
- receiving, by a detector, the continuous spectrum.

31. The method of claim 30, further comprising
- reflecting, via a second curved mirror, the pulsed light beam as a second light beam line,
- scanning the second light beam line across the sample to cause the sample to emit additional energy,
- dispersing the additional energy into second spectral components that form a second continuous spectrum area, the second continuous spectrum area corresponding to the second light beam line, and
- receiving, by the detector, the second continuous spectrum.

32. The method of claim 30, further comprising,
- outputting, by the detector, pixel data resulting from receiving the continuous spectrum and the second continuous spectrum;
- receiving, by an imaging module, the pixel data; and
- generating, via an imaging module one or more images based on the pixel data.

33. A method of generating a multi-dimensional, spectrally resolved image, the method comprising:
- generating a pulsed light beam;
- receiving, via a multi-beam generator, the pulsed light beam;
- emitting, by the multi-beam generator, multiple light beams in response to the pulsed light beam;
- simultaneously scanning the multiple light beams across a sample, the sample emitting energy corresponding to each of the multiple light beams;
- dispersing the emitted energy into spectral components that form continuous spectrum lines, each continuous spectrum line corresponding to one of the multiple light beams; and
- receiving, by a detector, each continuous spectrum line simultaneously.

34. The method of claim 33, further comprising,
- outputting, by the detector, pixel data resulting from receiving the continuous spectrum lines;
- receiving, by an imaging module, the pixel data; and
- generating, via the imaging module one or more images based on the pixel data.

\* \* \* \* \*